United States Patent [19]
Pearlman

[11] Patent Number: 6,055,452
[45] Date of Patent: *Apr. 25, 2000

[54] TISSUE CHARACTERIZATION BASED ON IMPEDANCE IMAGES AND ON IMPEDANCE MEASUREMENTS

[75] Inventor: Andrew L. Pearlman, Moshav Shorashim, Israel

[73] Assignee: Transcan Research & Development Co., Ltd., Ha'Emek, Israel

[*] Notice: This patent is subject to a terminal disclaimer.

[21] Appl. No.: 09/150,224

[22] Filed: Sep. 9, 1998

Related U.S. Application Data

[63] Continuation of application No. 08/725,927, Oct. 4, 1996, Pat. No. 5,810,742, which is a continuation-in-part of application No. PCT/US95/06141, May 19, 1995.

[30] Foreign Application Priority Data

| Oct. 24, 1994 | [IL] | Israel | 111381 |
|---|---|---|---|
| Apr. 20, 1995 | [IL] | Israel | 113454 |
| Oct. 5, 1995 | [IL] | Israel | 115525 |

[51] Int. Cl.$^7$ .................................................. A61N 1/00
[52] U.S. Cl. ............................................................ 600/547
[58] Field of Search ............................... 600/372, 382, 600/384, 386, 461, 476, 477, 478, 547; 601/21

[56] References Cited

U.S. PATENT DOCUMENTS

| 4,082,087 | 4/1978 | Howson . | |
| 4,291,708 | 9/1981 | Frei et al. . | |
| 4,387,721 | 6/1983 | Enjoji . | |
| 4,458,694 | 7/1984 | Sollish et al. . | |
| 4,510,939 | 4/1985 | Brenman et al. | 600/384 |
| 4,537,203 | 8/1985 | Machida . | |
| 4,539,640 | 9/1985 | Fry et al. . | |
| 4,617,939 | 10/1986 | Brown et al. . | |
| 4,763,660 | 8/1988 | Kroll et al. . | |

(List continued on next page.)

FOREIGN PATENT DOCUMENTS

| 0 000 759 | 2/1979 | European Pat. Off. . |
| 0 050 353 | 10/1981 | European Pat. Off. . |
| 0 190 043 | 8/1986 | European Pat. Off. . |
| 2 655 835 A1 | 6/1991 | France . |
| 42 25 112 C 1 | 12/1993 | Germany . |
| 2 138 148 | 10/1984 | United Kingdom . |
| 2 276 326 | 9/1994 | United Kingdom . |
| WO 91 13584 | 9/1991 | WIPO . |
| WO 94 20012 | 9/1994 | WIPO . |
| WO 96 12439 | 5/1996 | WIPO . |

OTHER PUBLICATIONS

Israeli Office Action.
G. Piperno et al., "Breast Cancer Screening by Impedance Measurements", Frontiers Med. Biol., vol. 2, 1990, pp. 111–117 plus two attached pages "Mammoscan: A Promising New Technology for Breast Screening and Diagnosis" and "Mammoscan Breast Impedance System".
Estelle et al., "Capacitive Sensors for In–Vivo Measurements of the Dielectric Properties of Biological–Materials", IEEE Trans. Inst. & Meas., vol. 37, No. 1, Mar. 1988, pp. 101–105.

(List continued on next page.)

*Primary Examiner*—George Manuel
*Attorney, Agent, or Firm*—William Squire, Esq.

[57] ABSTRACT

Apparatus for aiding in the identification of tissue type for an anomalous tissue in an impedance image comprising:

means for providing an polychromic immitance map of a portion of the body;

means for determining a plurality of polychromic measures from one or both of a portion of the body; and a display which displays an indication based on said plurality of polychromic measures.

14 Claims, 24 Drawing Sheets

U.S. PATENT DOCUMENTS

| | | |
|---|---|---|
| 4,805,621 | 2/1989 | Heinze et al. . |
| 4,819,658 | 4/1989 | Kolodner . |
| 4,823,797 | 4/1989 | Heinze et al. . |
| 4,896,673 | 1/1990 | Rose et al. . |
| 5,045,249 | 9/1991 | Jin et al. . |
| 5,063,937 | 11/1991 | Ezenwa et al. . |
| 5,070,862 | 12/1991 | Berlant ..................................... 601/21 |
| 5,099,846 | 3/1992 | Hardy . |
| 5,143,079 | 9/1992 | Frei et al. . |
| 5,178,147 | 1/1993 | Ophir et al. . |
| 5,247,938 | 9/1993 | Silverstein et al. . |
| 5,282,840 | 2/1994 | Hudrlik . |
| 5,295,483 | 3/1994 | Nowacki et al. . |
| 5,353,802 | 10/1994 | Ollmar . |
| 5,454,377 | 10/1995 | Dzwonczyk et al. . |

OTHER PUBLICATIONS

E. Gersing, "Messung der elecktrischen Impedance von Organen–Apparative Ausrustung fur Forschung und klinishe Anwendung", Bimed. Technik 36 (1991), pp. 6–11 (including abstract in english).

J. Vrana et al., "Mesure de l"Impedance des Tissus Hepatiqueles Transforms Pas des Processus Lesionels", Ann. Gastroentreaol. Hepetol., 1992, 28, No. 4, pp. 165–168 (including abstract in english).

V. Rajshekhar, "Continuous Impedance Monitoring During CT–Guided Stereotactic Surgery: Relative Value in Cystic and Solid Lesions", British journal of Neurosurgery (1992) 6, pp. 439–444.

J.J. Mastrototaro et al. "Rigid and Flexible Thin–Film Multi–Electrode Arrays for Transmural Cardiac Recording" IEEE Trans. Biomed. Engr., vol. 39, No. 3, Mar. 1992, pp. 271–279.

D.S. Buckles et al., "Image–Base Display of Activation Patterns Derived From Scattered Electrodes", IEEE Trans. Biomed. Engr., vol. 42, No. 1, Jan. 1995, pp. 111–115.

G.A. Urban et al., "Development of a Multiple Thin–Film Semimicro DC–Probe for Intracerebral Recordings" IEEE Trans. Biomed. Eng., vol. 37, No. 10, Oct. 1990, pp. 913–917.

R.W.M. Smith et al., "A Real–Time Electrical Impedance Tomography System for Clinical Use–Design and Preliminary Results", IEEE Trans. Biomed. Eng., vol. 42, Feb. 1995, pp. 133–139.

A.J. Surowiec et al., Dielectric Properties of Breast Carcinoma and the Surrounding Tissues:, IEEE Trans. Biomed. Eng., vol. 35, No. 4, Apr. 1988, pp. 257–263.

M. Heimbach "Measures of Performance", Electrical Impedance Tomography, (12.1), 1990, pp. 158–174.

R.J. Davies et al., "Detection of the Cancer–Prone Colon, using Transepothelial Impedance Analysis", Arhc Surg., vol. 124, Apr. 1989, pp. 480–484.

T. Morimoto et al., "A Study of the Electrical Bio–Impedance of Tumors", Journal. of Investigative Surgery, vol. 6, 1993, pp. 25–32.

Man et al., "Results of Pre–Clinical Test for Breast Cancer Detection by Dielectric Measurements", International Conference of Medical and Biological Engineering, V International Conference of Medical Physics, 30.4, Jerusalem, Israel, Aug. 12–24, 1979.

International Search Report.

Internation Preliminary Examination Report.

Written Opinion.

Masuda et al: "Topographical Map of Innervation Zones within Single Motor Units Measured with a Grid Surface Electrode" I.E.E.E. Transactions on Biomedical Engineering vol. 35, No. 8, Aug. 1988 (Aug. 1988), pp. 623–628, XP000005699 New York, US p. 623, right hand column, line 24–line 35 figures 1, 2.

Monster et al: "A System for the Rapid Acquisition of Surface Potential Maps of Human Skeletal Muscle Motor Units" I.E.E.E. Transactions on Biomedical Engineering vol. 27, No. 2, Feb. 1980 (Feb. 1980) pp. 110–112, XP002114215 New York, US p. 111, left hand column line 65 right hand column line 22 figure 1.

Riu et al: "In Vivo Static Imaging for the Reactive Parts in Electrical Impedance Tomography Using Multifrquency Techniques" Proceedings of the Annual International Conference of the Engineering in Medicine and Biology Society vol. 5, No. 14, Oct. 1992 (Oct. 1992), pp. 1706–1707, XP000514393 US.

Cespedes et al: "Elastography: Elastic Imaging Using Ultrasound With Application to Muscle and Breast In Vivo" Ultrasonic Imaging vol. 15, No. 2, Apr. 1993 (Apr. 1993) pp. 73–88 XP000383142 Orlando, US.

Eyuboglu et al: "In Vivo Imaging of Cardiac Related Impedance Changes" I.E.E.E. Engineering in Medicine and Biology vol. 8, No. 1, Mar. 1989 (Mar. 1989) pp. 39–45 XP000002279 New York, US.

Record et al: "Multifrequency Electrical Impedance Tomography" Clinical Physics and Physiological Measurement, Suplement A vol. 13, Jul. 1992 (Jul. 1992) pp. 47–50 XP000431598 York, GB.

Zhili Huang et al: "Bioimpedance Measurement: Theory, Experiment and Application" Proceedings of the Ninth Annual Conference of the IEEE Engineering in Medicine and Biology Society vol. 3, Nov. 1987 (Nov. 1987) pp. 1416–1427 XP000015434.

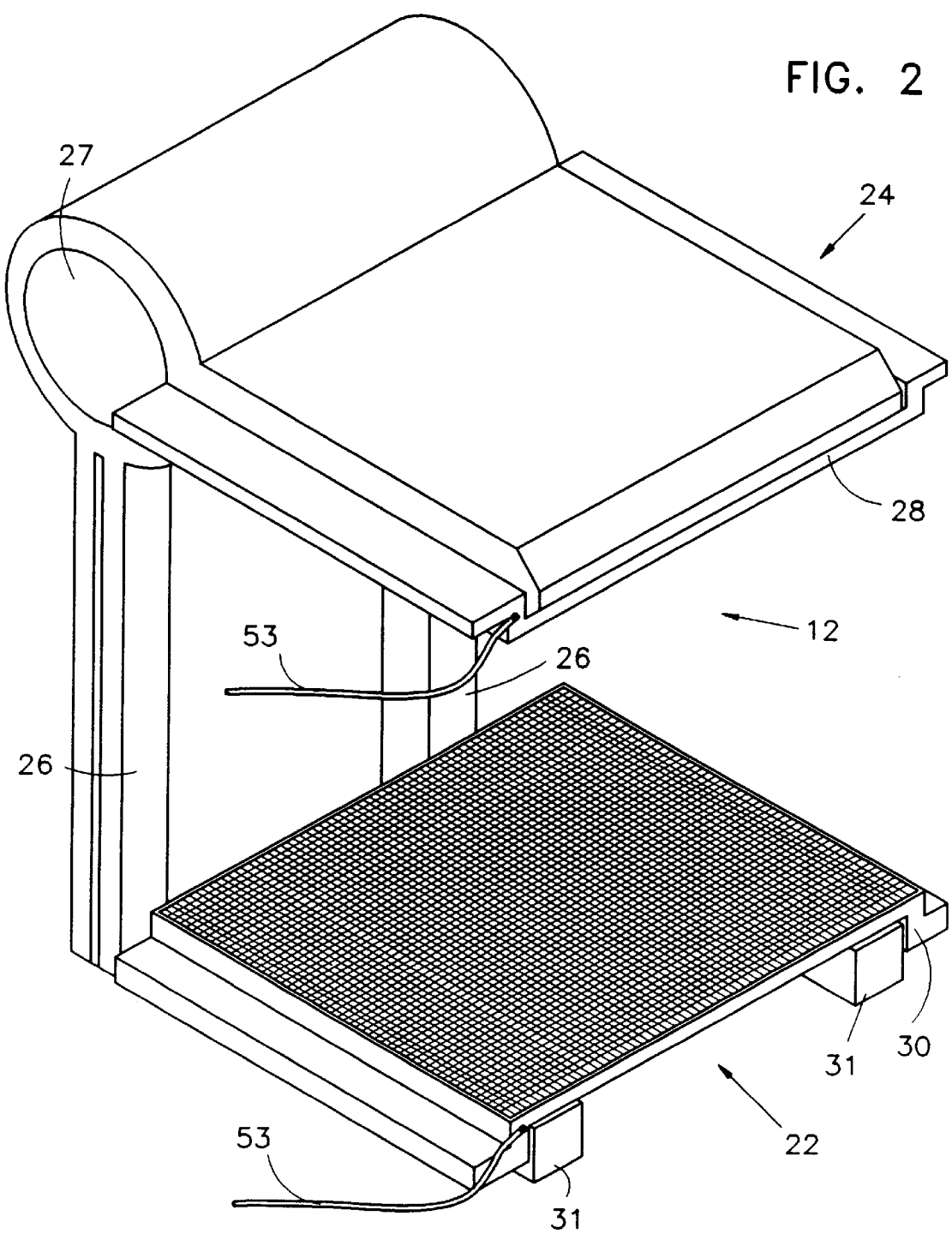

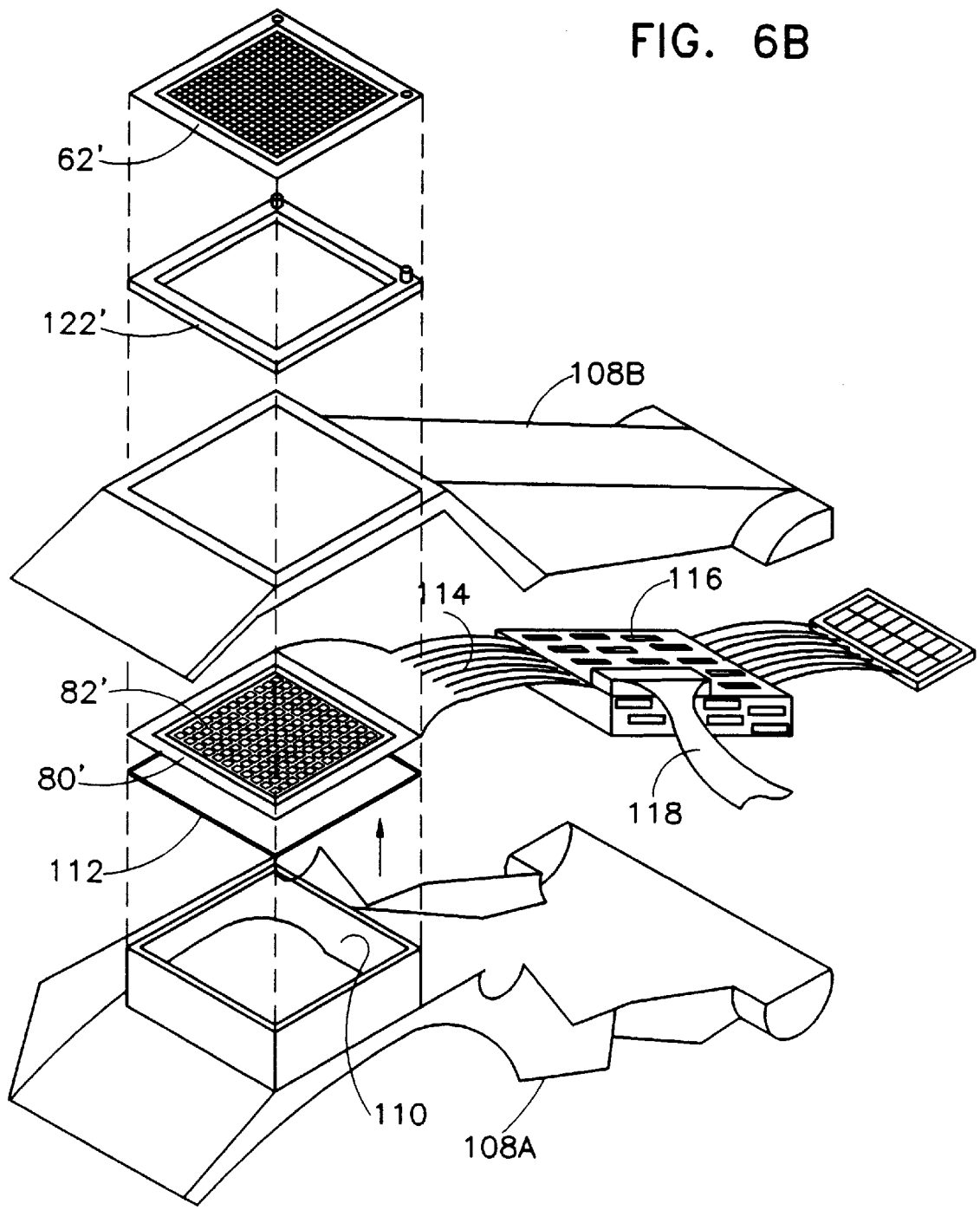

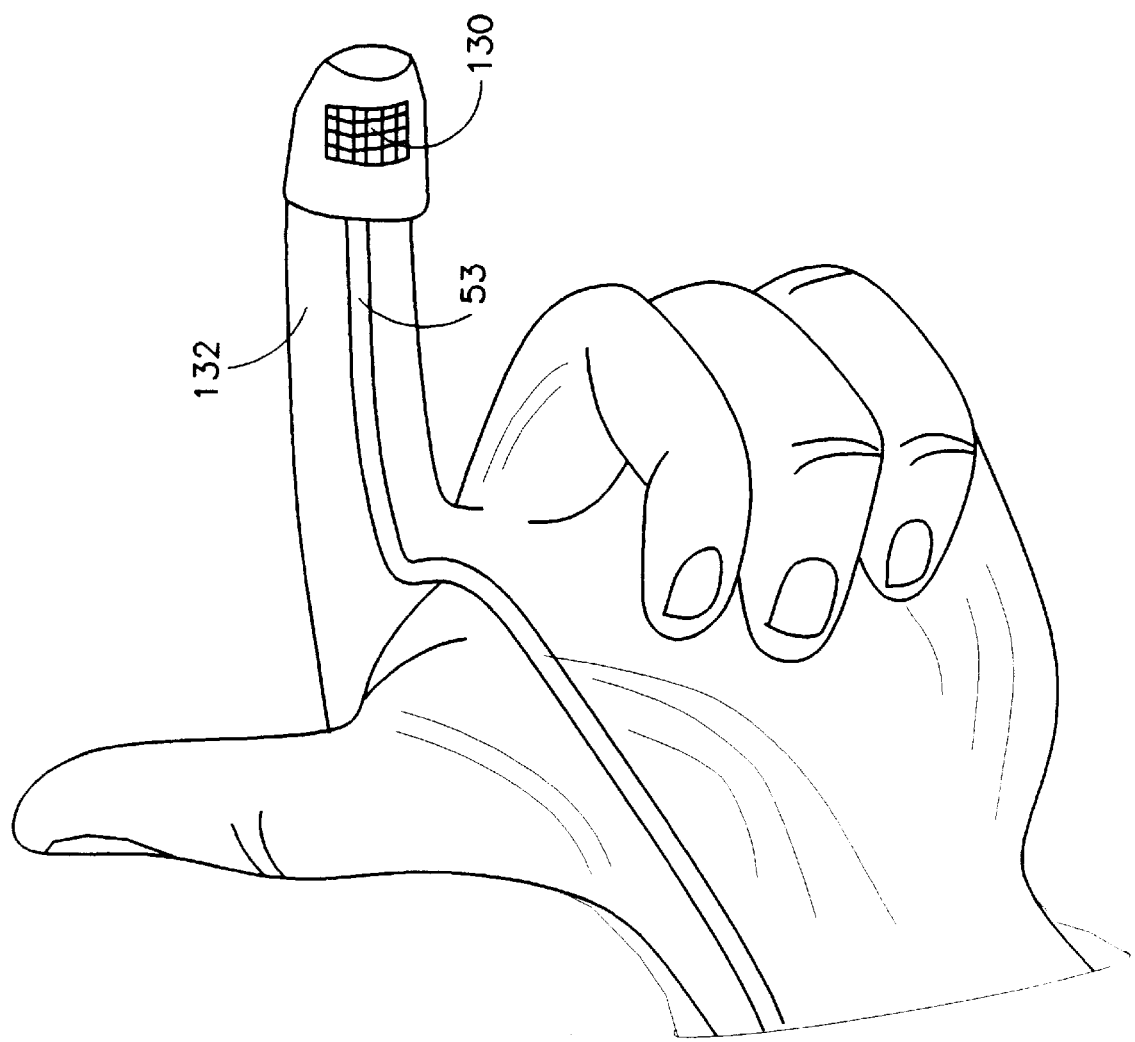

TISSUE CHARACTERIZATION BASED ON IMPEDANCE IMAGES AND ON IMPEDANCE MEASUREMENTS

CROSS REFERENCE TO RELATED APPLICATION

This application is a continuation of application Ser. No. 725,927 filed Oct. 4, 1996, now U.S. Pat. No. 5,810,742.

This application is a Continuation-in-Part of International Application No. PCT/US95/06141, filed May 19, 1995, the disclosure of which is incorporated by reference in its entirety.

FIELD OF THE INVENTION

The present invention relates to systems for tissue characterization based on impedance measurement at a point or at an array of points.

BACKGROUND OF THE INVENTION

The measurement of electrical potentials on the skin has many uses. For example, electrocardiograms are derived from measuring the potential generated by the heart of a patient at various points on the skin.

Skin potentials are also measured in apparatus for determining the electrical impedance of human tissue, including two-dimensional (e.g., U.S. Pat. Nos. 5,063,937, 4,291,708 and 4,458,694) or three-dimensional (e.g., U.S. Pat. Nos. 4,617,939 and 4,539,640) mapping of the tissue impedance of the body. In such systems an electrical potential is introduced at a point or points on the body and measured at other points at the body. Based on these measurements and on algorithms which have been developed over the past several decades, an impedance map or other indication of variations in impedance can be generated.

U.S. Pat. Nos. 4,291,708 and 4,458,694 and "Breast Cancer screening by impedance measurements" by G. Piperno et al. Frontiers Med. Biol. Eng., Vol. 2, pp 111–117, the disclosures of which are incorporated herein by reference, describe systems in which the impedance between a point on the surface of the skin and some reference point on the body of a patient is determined. These references describe the use of a multi-element probe for the detection of cancer, especially breast cancer, utilizing detected variations of impedance in the breast.

In these references a multi-element probe is described in which a series of flat, stainless steel, sensing elements are mounted onto a PVC base. A lead wire is connected between each of these elements and detector circuitry. Based on the impedance measured between the elements and a remote part of the body, signal processing circuitry determines the impedance variations in the breast. Based on the impedance determination, tumors, and especially malignant tumors, can be detected.

The multi-element probe is a critical component in this system and in other systems which use such probes. On one hand the individual elements must make good contact with the skin and with the corresponding points on the sensing or processing electronics while also being well isolated from each other. On the other hand, use of gels to improve skin contact carries the risk of cross-talk, dried gel build-up on the elements and inter-patient hygienic concerns.

A paper titled "Capacitive Sensors for In-Vivo Measurements of the Dielectric Properties of Biological materials" by Karunayake P. A. P. Esselle and Stanislaw S. Stuchly (IEEE Trans. Inst & Meas. Vol. 37, No. 1, p. 101–105) describes a single element probe for the measurement of in vivo and in vitro measurements of the dielectric properties of biological substances at radio and microwave frequencies. The sensor which is described is not suitable for impedance imaging.

A paper entitled "Messung der elektrischen Impedance von Organen—Apparative Ausrüstung für Forschung und klinishe Anwendung" by E. Gersing (Biomed. Technik 36 (1991), 6–11) describes a system which uses single element impedance probes for the measurement of the impedance of an organ. The device described is not suitable for impedance imaging.

A Paper titled "MESURE DE L'IMPEDANCE DES TISSUS HEPATIQUELES TRANSFORMES PAS DES PROCESSUS LESIONELS" by J. Vrana et al. (Ann. Gastroentreol. Hepetol., 1992, 28, no. 4, 165–168) describes a probe for assessing deep tissue by use of a thin injection electrode. The electrode was positioned by ultrasound and specimens were taken for cytological and histological assessment. The electrode was constituted on a biopsy needle used to take the samples.

A paper titled "Continuous impedance monitoring during CT-guided stereotactic surgery: relative value in cystic and solid lesions" by V. Rajshekhar (British Journal of Neurosurgery (1992) 6, 439–444) describes using an impedance probe having a single electrode to measure the impedance characteristics of lesions. The objective of the study was to use the measurements made in the lesions to determine the extent of the lesions and to localize the lesions more accurately. The probe is guided to the tumor by CT and four measurements were made within the lesion as the probe passed through the lesion. A biopsy of the lesion was performed using the outer sheath of the probe as a guide to position, after the probe itself was withdrawn.

A paper titled "Rigid and Flexible Thin-Film Multielectrode Arrays for Transmural Cardiac Recording" by J. J. Mastrototaro et al. (IEEE TRANS. BIOMED. ENG. Vol. 39, No. 3, March 1992, 271–279) describes a needle probe and a flat probe each having a plurality of electrodes for the measurement of electrical signals generated in the heart.

A paper entitled "Image-Based Display of Activation Patterns Derived from Scattered Electrodes" by D. S. Buckles et al. (IEEE TRANS. BIOMED ENGR. Vol. 42, No. 1, January 1995, 111–115) describes a system for measurement of electrical signals generated on the heart by use of an array of electrodes on a substrate. The heart with the electrodes in place is viewed by a TV camera and an operator marks the positions of the electrodes on a display. The system then displays the heart (as visualized prior to the placement of the electrodes) with the position markings.

A paper entitled "Development of a Multiple Thin-Film Semimicro DC-Probe for Intracerebral Recordings" by G. A. Urban et al. (IEEE TRANS. BIOMED ENGR. Vol. 37, No. 10, October 1990, 913–917) describes an elongate alumina ceramic probe having a series of electrodes along its length and circumference for measuring functional parameters (electrical signals) in the brain. Electrophysiological recording, together with electrostimulation at the target point during stereotactic surgery, was performed in order to ensure exact positioning of the probe after stereotactic calculation of the target point. Bidimensional X-Ray imaging was used in order to verify the exact positioning of the electrode tip.

SUMMARY OF THE INVENTION

It is an object of certain aspects of the invention to provide a multi-element probe having improved and more uniform and repeatable contact with the skin with minimal operator expertise and minimal risk of cross-patient contamination.

It is an object of certain aspects of the invention to provide improved inter-element electrical isolation, and to permit sliding of the probe while it is urged against the skin.

It is an object of certain aspects of the invention to provide a relatively inexpensive disposable multi-element probe.

It is an object of certain aspects of the invention to provide a multi-element probe having sufficient transparency to allow for viewing of tissue surface features and to allow for referencing the probe with respect to physical features of or on the skin.

It is an object of certain aspects of the invention to provide a method of distinguishing between artifacts and abnormalities.

It is an object of certain aspects of the invention to provide a system for electrical impedance imaging which simultaneously acquires, uses and preferably displays both capacitance and conductance information.

It is an object of certain aspects of the invention to provide a system for electrical impedance testing of the breast or other body region which provides more accurate information regarding the position of impedance abnormalities detected in the breast or other region.

It is an object of certain aspects of the invention to provide for electrical impedance testing with a variable spatial resolution.

It is an object of certain aspects of the invention to provide for two dimensional electrical impedance testing giving an indication of the distance of an abnormality from the surface of the skin.

It is an object of certain aspects of the invention to provide apparatus especially suitable for breast impedance measurements.

It is an object of certain aspects of the invention to provide guidance for placement of elongate objects such as biopsy needles, localization needles, fiber optic endoscopes and the like using real time and/or recorded stereotactic images to guide the object.

It is a further object of certain aspects of the invention to provide a biopsy needle having an impedance measuring function to aid in the taking of a biopsy.

It is an object of certain aspects of the invention to provide more direct comparison between the results of electrical impedance maps and the results of optical, ultrasound or other imaging modalities.

It is an object of certain aspects of the invention to provide apparatus and method for indicating, on an anatomical illustration, the location and region from which an impedance image, shown together with the illustration is derived.

It is an object of certain aspects of the invention to provide apparatus which facilitates direct comparison between X-Ray and impedance mammographic images, as for example by superposition of the images.

It is an object of certain aspects of the invention to provide a method of determining a polychromic (multi-frequency) impedance map.

It is an object of certain aspects of the invention to optimize the impedance mapping utilizing a pulsed voltage excitation.

It is an object of certain aspects of the invention to provide palpation and tactile sensing of an area while simultaneously providing an impedance image of the area.

It is an object of certain aspects of the invention to allow for the identification of tissue types from impedance maps.

In general, the term "skin" as used herein means the skin or other tissue of a subject.

The present inventor has found that when, in an impedance image, an anomaly is perceived, the type of tissue underlying the position of the anomaly on the image may generally be determined by a characterization procedure which includes the determination of a number of polychromic measures for the anomaly and surrounding non-anomalous tissue and comparison of the measures with ranges of values of individual polychromic measures or their combinations which are characteristic of various types of tissue. It has been found that normal tissue such as breast tissue, nipples and the infra-mammary ridge, ribs and Costochondral Junctions and benign hyperplasia can generally be distinguished from cancerous tumors and precancerous atypical hyperplasia. These measures are based on the structure and form of the deviation of the capacitance and conductance of the anomalous portion of the image from that of the surrounding, normal tissue. For those cases where there is some ambiguity between some types of tissue, knowledge of the anatomy of the imaged area or palpation of the area can often remove the ambiguity or additional views can be taken to remove the ambiguity.

In an image the measures are preferably determined by comparing the capacitance or conductance of the anomalous pixels on the image to be characterized with the capacitance or conductance of normative tissue around the mean or median value of the capacitance or conductance, typically in terms of quantified deviation of a given pixel or region from the median in the image, as measured in multiples of the estimated standard deviation or coefficient of variance.

The method is also potentially useful to determine tissue types in situations where either a single impedance probe is used or where the image is small and only anomalous areas are imaged. In these cases the comparison is made between the values of capacitance or conductance measured for the anomalous region as compared to the capacitance or conductance measured for a nearby region known to be normal.

As used herein the term immitance means either the complex admittance or impedance. Furthermore the term polychromic measure is a measure which is based on the immitance or on the real or imaginary part thereof or on a combination of the immitance and/or the real part thereof and/or the imaginary part thereof at a plurality of frequencies, i.e., on the spectrum thereof.

There is therefore provided, in accordance with a preferred embodiment of the invention apparatus for aiding in the identification of tissue type for an anomalous tissue in an impedance image comprising:

means for providing an polychromic immitance map of a portion of the body;

means for determining a plurality of polychromic measures, preferably normalized measures, of an anomalous region of the immitance image; and a display which displays an indication based on said plurality of polychromic measures.

Preferably the apparatus includes means for providing a map of said polychromic measures and wherein said indication includes a display of a plurality of said maps.

In a preferred embodiment of the invention the display includes an overlay of maps of said polychromic measures.

Preferably the apparatus includes means for matching the values of the plurality of measures with predetermined values of the measures to identify the tissue type of the anomalous tissue.

In one preferred embodiment of the invention the indication is the display of a map of said determined tissue type.

There is further provided, in accordance with a preferred embodiment of the invention, apparatus for determining a tissue type for an anomalous tissue comprising:

means for determining a plurality of polychromic measures of the anomalous tissue; and means for matching the values of the plurality of measures with predetermined values of the measures to identify the tissue type of the anomalous tissue.

There is further provided, in accordance with a preferred embodiment of the invention, a method of determining a tissue type for tissue in an anomalous region in an immitance image, comprising:

determining a plurality of polychromic measures, preferably normalized measures, of said anomalous region; and matching the values of the plurality of measures to identify the tissue type of the anomalous region.

There is further provided, in accordance with a preferred embodiment of the invention, a method of determining a tissue type for an anomalous tissue:

determining a plurality of polychromic measures, preferably normalized measures, of the anomalous tissue;

matching the values of the plurality of measures with predetermined values to identify the tissue type of the anomalous tissue.

Preferably, one of the polychromic measures is derived from the sum, over a plurality of frequencies, of the positive deviations of the capacitance of the anomaly from that of typical nonanomolous regions.

Preferably, one of the polychromic measures is derived from the sum, over a plurality of frequencies, of the negative deviations of the capacitance of the anomaly from that of typical nonanomolous regions.

Preferably, one of the polychromic measures is derived from the sum, over a plurality of frequencies, of the positive deviations of the conductance of the anomaly from that of typical nonanomolous regions.

Preferably one of the measures is the integral of the phase or the sum of phase values over a range of frequencies.

Preferably, one of the measures is the difference between the integral of the difference between the phase at a point and the mean or median value of the phase in the image, over a range of frequencies.

Preferably, one of the measures is the derivative of the capacitance curve or its logarithm as a function of frequency, evaluated at a given frequency.

Preferably, one of the measures is the derivative of the conductance curve or its logarithm as a function of frequency, evaluated at a given frequency.

Preferably, one of the measures is a frequency at which the phase of the impedance reaches a specified value, preferably 45 degrees.

BRIEF DESCRIPTION OF THE DRAWINGS

The invention will be more fully understood and appreciated from the following detailed description, taken in conjunction with the drawings in which:

FIG. 2 is a perspective view of an imaging head suitable for breast impedance mapping in accordance with a preferred embodiment of the invention;

FIG. 6B shows a partially expanded bottom view of the probe of FIG. 6A, in accordance with a preferred embodiment of the invention;

FIG. 7A is a perspective view of a fingertip probe in accordance with a preferred embodiment of the invention;

DETAILED DESCRIPTION OF THE PREFERRED EMBODIMENTS

Figure 1:
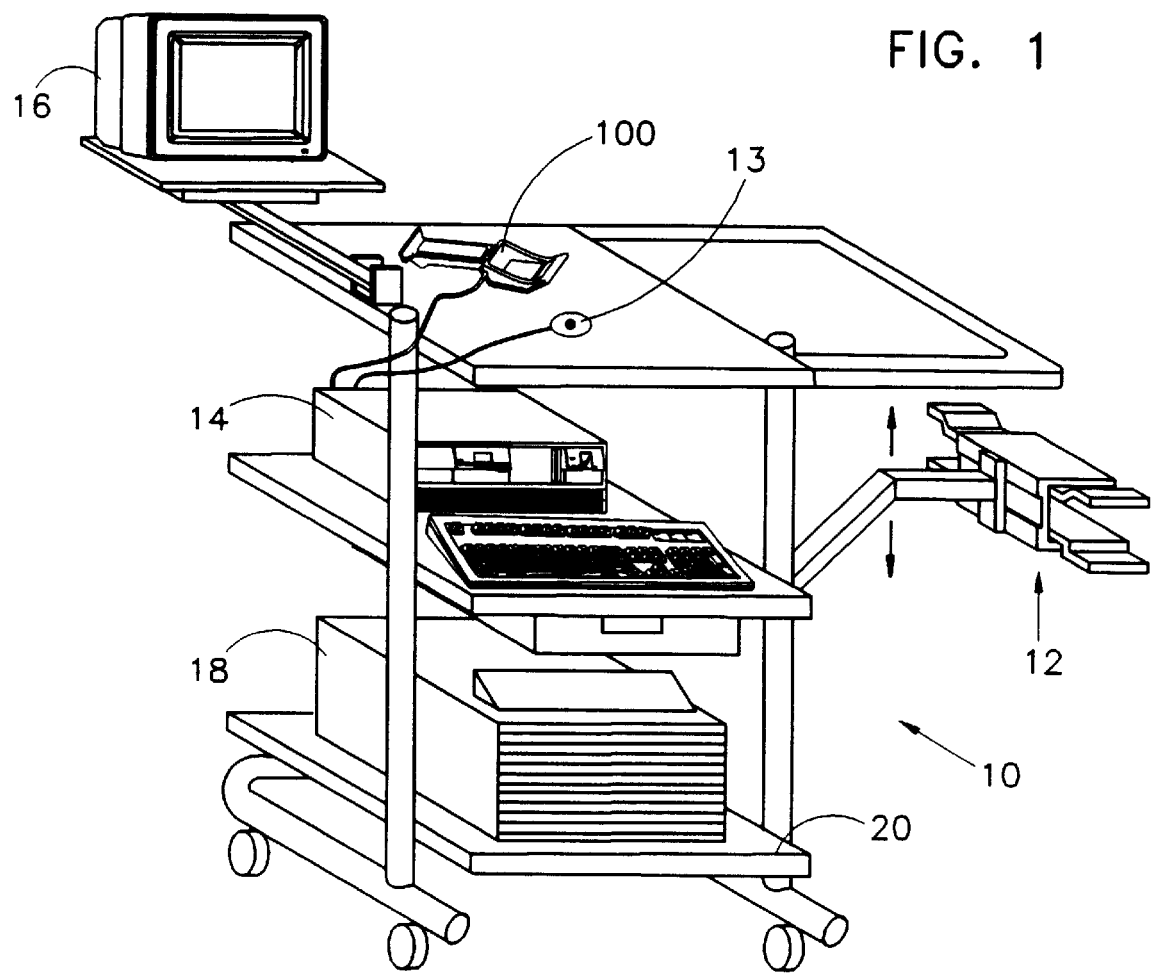
FIG. 1 is an overall view of an impedance mapping system especially suitable for breast impedance mapping in accordance with a preferred embodiment of the invention.

Reference is made to FIGS. 1 and 2 which illustrate an impedance mapping device 10 suitable for mapping the impedance of a breast.

Mapping device 10 includes an imaging head 12, which is described below, which holds the breast and provides contact therewith for providing electrical excitation signals thereto and for receiving resultant electrical signals therefrom. Signals to and from the head are generated and received by a computer/controller 14 which produces impedance maps of the breast under test for display on a monitor 16. The impedance maps may be stored in computer/controller 14 for later viewing or processing or hard copies may be provided by a hard copy device 18 which may be a laser printer, video printer, Polaroid or film imager or multi-imager.

The entire mapping device 10 may be conveniently mounted on a dolly 20 to facilitate placement of the imaging head with respect to the patient.

FIG. 1 also shows a hand held probe 100, described in more detail below, and a reference probe 13.

FIG. 2 shows imaging head 12 in more detail. Head 12 comprises a movable lower plate probe 22 and a stationary upper plate probe 24 which is mounted on a pair of rails 26 to allow the distance between plate probes 22 and 24 to be varied.

Movement of plate probe 22 along rails 26 may be achieved either by a motor (not shown) including suitable protection against over-pressure as is traditional in X-ray breast imaging, or by hand.

Either or both of plate probes 22 and 24 are provided with multi-element probes 28 and 30 respectively, which are described more fully below, which electrically contact the breast with a plurality of sensing elements to optionally provide electrical excitation to the breast and to measure signals generated in response to the provided signals. Alternatively, electrical excitation to the breast is provided by reference probe 13 which is placed on the arm, shoulder or back of the patient, or other portion of the patient.

In practice, a breast is inserted between probes 28 and 30 and plate probe 24 is lowered to compress the breast between the probes. This compression reduces the distance between the probes and provides better contact between the sensing elements and the skin of the breast. Although compression of the breast is desirable, the degree of compression required for impedance imaging is much lower than for X-Ray mammography, and the mapping technique of the present invention is typically not painful.

Alternatively or additionally, the probes are curved to conform with the surface of the breast.

Head 12 is provided with a a pivot (not shown) to allow for arbitrary rotation of the head about one or more of its axes. This allows for both medio-lateral and cranio-caudal maps of the breast to be acquired, at any angular orientation about the breast. Preferably, head 12 may be tilted so that the surfaces of plate probes 22 and 24 are oriented with a substantial vertical component so that gravity assists the entry of the breast into the space between the maximum extent and to keep it from inadvertently falling out. This is especially useful when the patient leans over the plates so that her breasts are positioned downwardly between the plate probes.

Furthermore, in a preferred embodiment of the invention, one or both of probes 28 and 30 may be rotated about an axis at one end thereof, by a rotation mechanism 27 on their associated plate probes 22 or 24, such as is shown in FIG. 2 for probe 28. Additionally or alternatively, probes 28 and/or 30 may be slidable, as for example along members 31.

Such additional sliding and rotating flexibility is useful for providing more intimate skin contact of the probes with the breast, which has a generally conical shape. Furthermore, such flexibility allows for better imaging of the areas of the breast near the chest wall or the rib cage, which are extremely difficult to image in x-ray mammography.

Figure 3A:
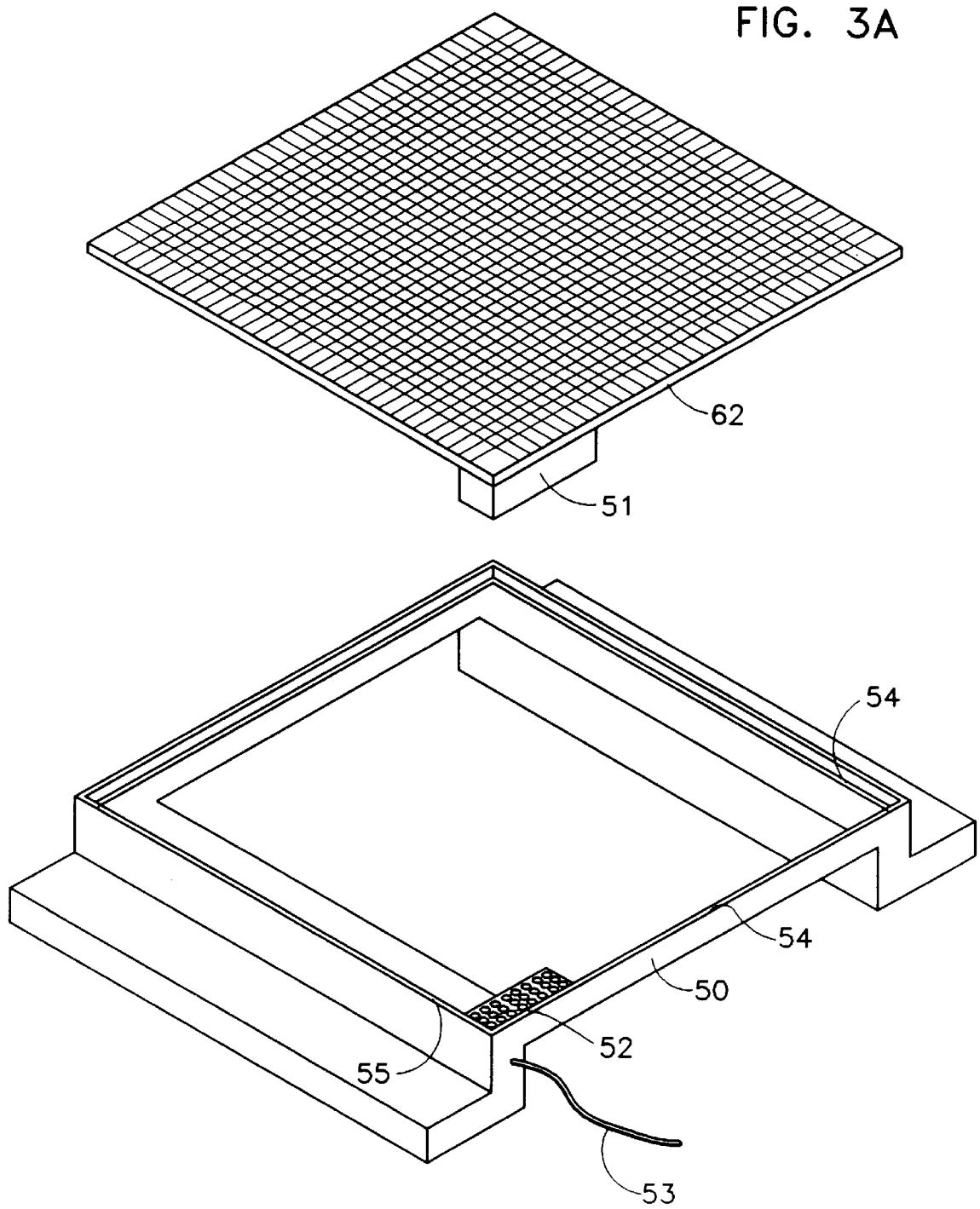
FIGS. 3A and 3B show partially expanded views of two preferred probe head configurations suitable for use in the imaging head of FIG. 2.
Figure 3B:
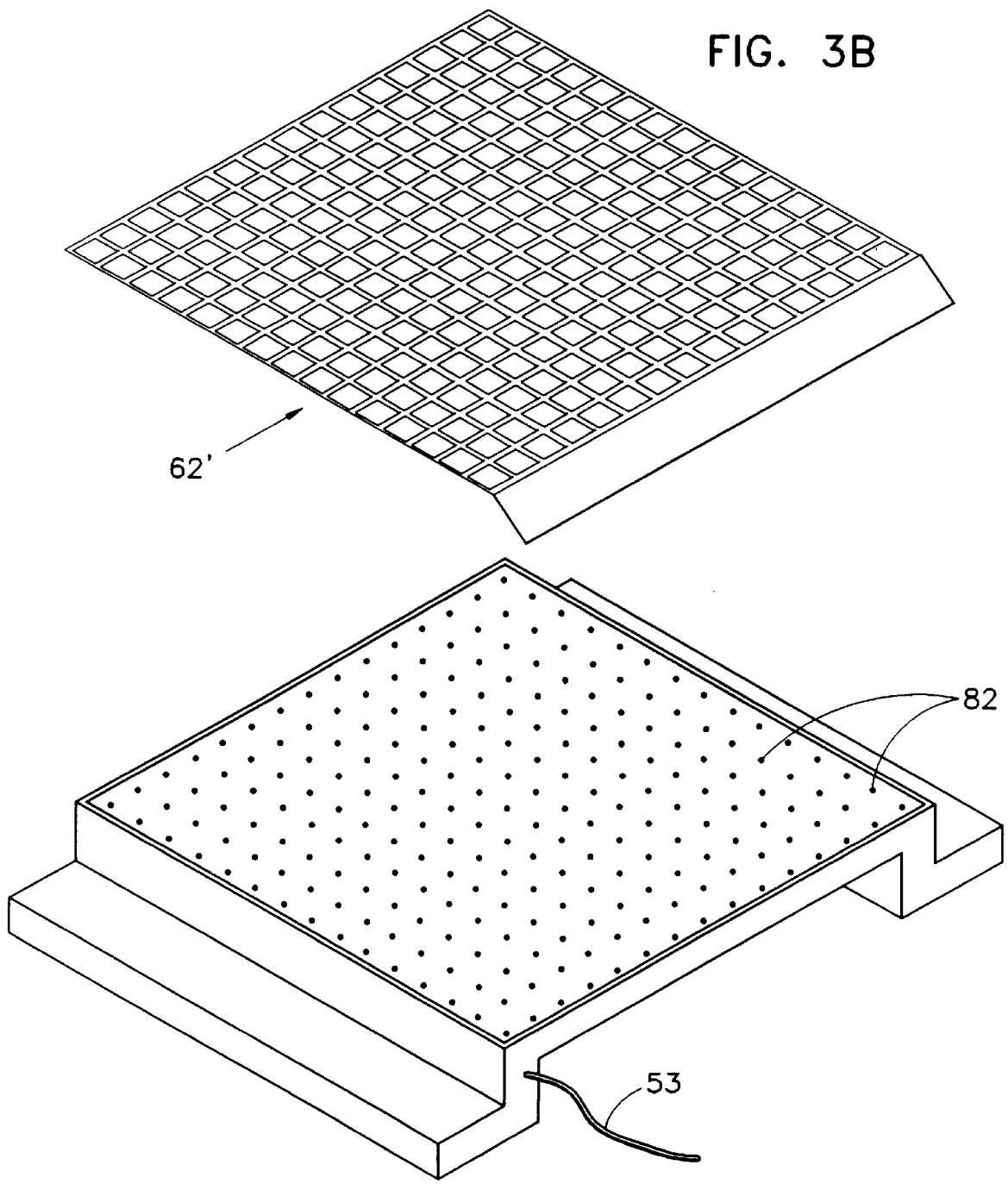

FIGS. 3A and 3B show partially expanded views of two probe head configurations suitable for use in the imaging head of FIG. 2, in accordance with preferred embodiments of the invention.

In the embodiment of FIG. 3A, a preferably removable multi-element probe 62, which is described below in more detail, is attached to a probe head base 50 via a pair of mating multi-pin connectors 51 and 52. A cable 53 couples connector 52 to computer 14. When multi-element probe 62 is inserted into base 50 (that is to say, when connector 51 is fully inserted into connector 52), the relatively stiff bottom of probe 62 rests on ledges 54 formed in the base, such that the surface 55 of the base and the surface of element 62 are preferably substantially coplanar.

In the embodiment of FIG. 3B, a series of contacts 82 are formed on base 50 and a disposable multi-element probe 62' is attached to the contacts as described below with reference to FIGS. 5A and 5B. Cable 53 couples the contacts to computer 14.

Figure 4:
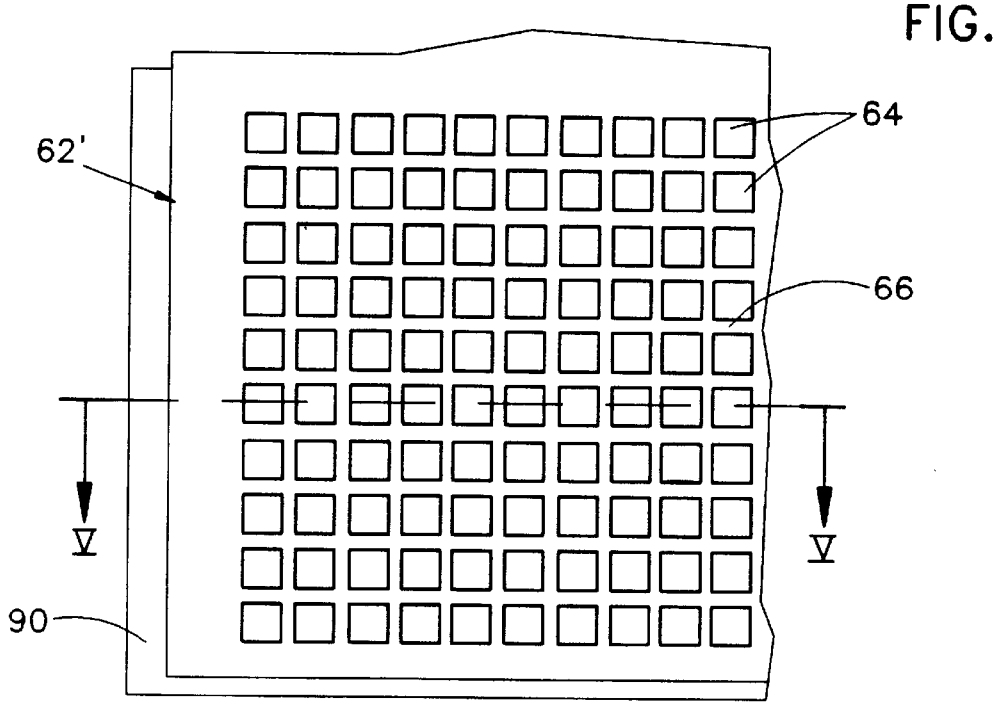
FIG. 4 is a top view of a portion of a multi-element probe in accordance with a preferred embodiment of the invention.
Figure 5A:
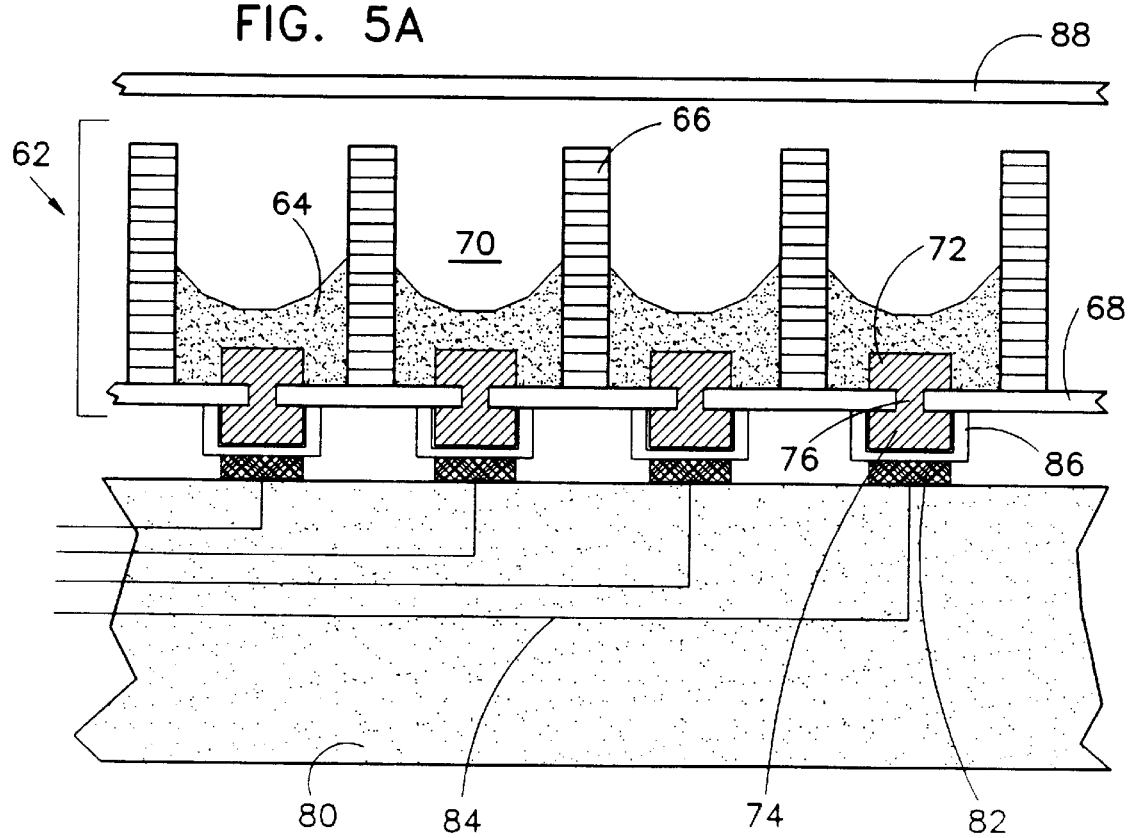
FIG. 5A is a partial, partially expanded cross-sectional side view of the probe of FIG. 4 along lines V—V, suitable for the probe head configuration of FIG. 3B.
Figure 5B:
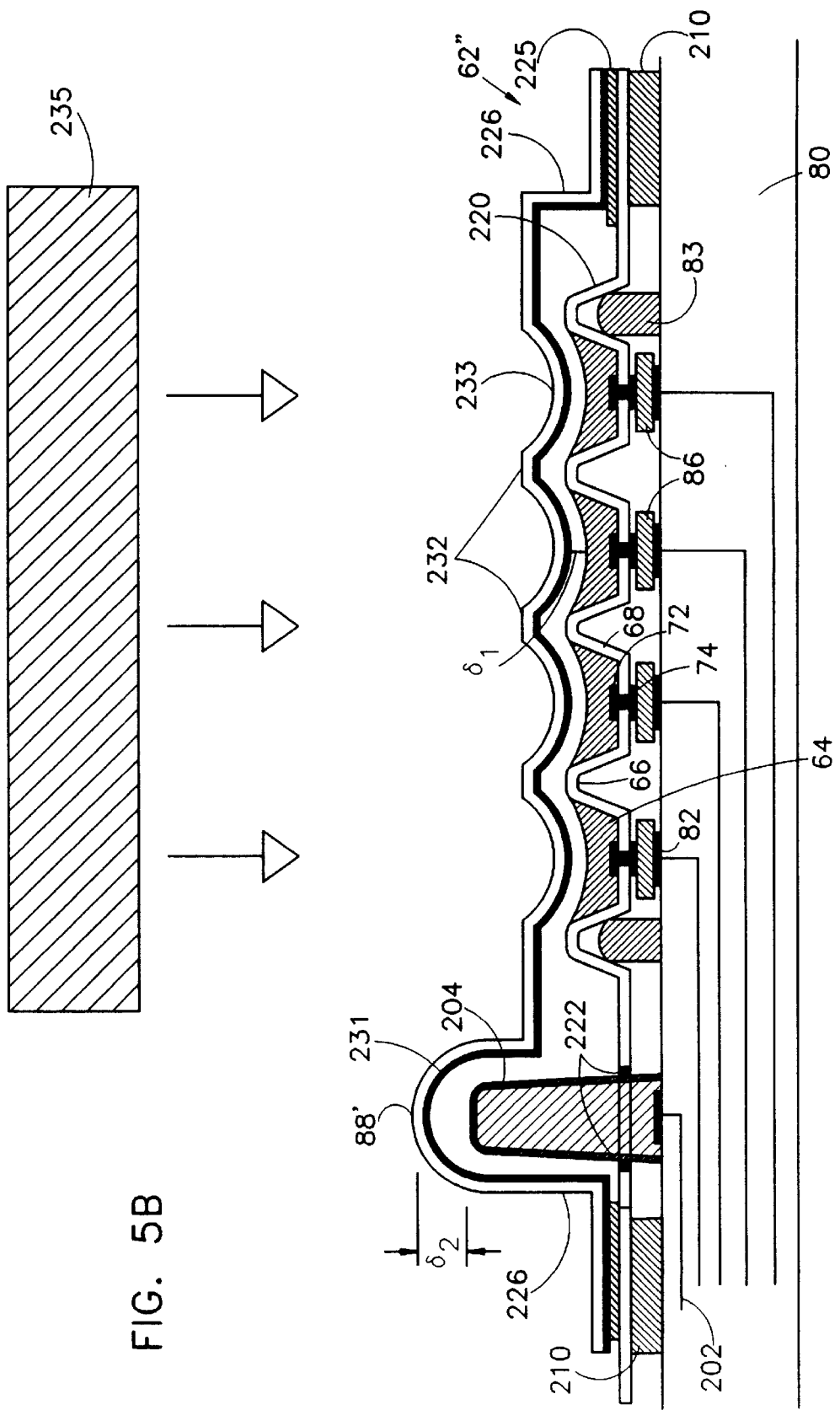
FIG. 5B is a partially expanded cross-sectional side view of an alternative probe in accordance with a preferred embodiment of the invention.

FIGS. 4, 5A and 5B show top and side views of a portion of multi-element probe 62' and contacts 74, while FIGS. 5A and 5B show a partially expanded cross-sectional side view of probe 62' along lines V—V. While the embodiment shown in FIGS. 4, 5A and 5B is especially suitable for the probe head configuration of FIG. 3B, much of the structure shown in these FIGS. 5 is common to multi-element probes used in other configurations described herein.

As shown in FIGS. 4, 5A and 5B, disposable multi-element probe 62' preferably incorporates a plurality of sensing elements 64, separated by separator or divider elements 66.

As shown more clearly in FIGS. 5A and 5B, sensing elements 64, comprise a bio-compatible conductive material (for example Neptrode E0751 or Neptrode E0962 Hydrogel distributed by Cambrex Hydrogels, Harriman, N.Y.) such as is sometimes used for ECG probes in a well 70 formed by a first, front, side of a mylar or other flexible, non-conducting substrate 68, such as a thin mylar sheet and the divider elements 66. A suitable thickness for the mylar sheet is approximately 0.2 mm for probe 62'. The substrate is preferably pierced in the center of each well. The hole resulting from the piercing is filled with a conducting material which is also present on the bottom of well 70 and on a second, back, side of substrate 68 to form a pair of electrical contacts 72 and 74 on either side of the substrate and an electrically conducting feed-through 76 between the pair of contacts. As shown, a separate contact pair and feed-through is provided for each sensing element.

Alternatively, the substrate may be formed of any suitable inert material including plastics such as polyethylene, polypropylene, PVC, etc.

Wells 70 may be formed in a number of ways. One method of forming the wells is to punch an array of square holes in a sheet of plastic, such as polypropylene, which is about 0.2–1 mm thick. This results in a sheet containing only the divider elements. This sheet is bonded to substrate 68 which has been pre-pierced and in which the contacts and feed-throughs have been formed. Another method of forming the wells is to emboss a substrate containing the contacts and feed-throughs to form divider elements in the form of ridges which protrude from the substrate as shown in FIG. 5B. Yet another method of producing the wells is by printing the well walls using latex based ink or other bio-compatible material having a suitable firmness and flexibility. Another method of production is by injection molding of the substrate together with the divider elements. And yet another method of producing the wells is by laminating to the substrate a preformed grid made by die cutting the array of divider elements in a sheet of plastic, injection molding, or other means.

The conductors and feed-throughs may be of any conductive material which will provide reliable feed-through plating of the holes. One method of manufacturing the contacts and holes is by screen printing of the contacts on both sides of the substrate. If conductive paste having a suitable viscosity is used, the paste will fill the hole and form a reliable contact between contacts 72 and 74. Although many conductive materials can be used, non-polarizing conductors, such as silver/silver chloride are preferred. A conductive paste suitable for silk screening the conductors onto the substrate is Pad Printable Electrically conductive Ink No. 113-37 manufactured and sold by Creative Materials Inc., Tyngsboro, Mass.

In general contacts 72 and 74 are only 10–200 microns thick and wells 70 are generally filled with conductive viscous gel material or hydrogel material to within about 0.2 mm of the top of the dividing elements. In general, if low separators are used, the hydrogel may be omitted. However, in the preferred embodiment of the invention, the wells are at least partially filled by hydrogel or a similar material.

Hydrogel is available in both UV cured and heat cured compositions. In either case a measured amount of uncured semi-liquid hydrogel is introduced into each well and the hydrogel is cured. Alternatively, the wells are filled with the uncured material and a squeegee which is pressed against the top of the divider elements with a predetermined force is moved across the top of the divider elements. This will result in the desired gap between the top of the hydrogel and the top of the wells.

In an alternative embodiment of the invention, the hydrogel material is replaced by a sponge material or similar supportive matrix impregnated with conductive viscous gel or the well is simply filled with the conductive gel to the desired height.

During use of the probe, the probe is urged against the skin which is forced into the wells and contacts the hydrogel or alternative conductive material. Optionally, a somewhat viscous conductive gel, such as Lectron II Conductivity Gel (Pharmaceutical Innovations, Inc. Newark, N.J.), may be used to improve contact with the skin. In this case, the dividing elements will reduce the conduction between the cells such that the substantial independence of the individual measurements is maintained. Alternatively, the conductive gel may be packaged together with the probe, with the conductive gel filling the space between the top of the hydrogel and the top of the wells. The use of a conductive gel is preferred since this allows for sliding movement of the probe and its easy positioning while it is urged against the skin. The separators substantially prevent the conductive gel from creating a low conductance path between adjoining sensing elements and also keep the hydrogel elements from touching each other when the probe is applied to the skin with some pressure.

Figure 5C:
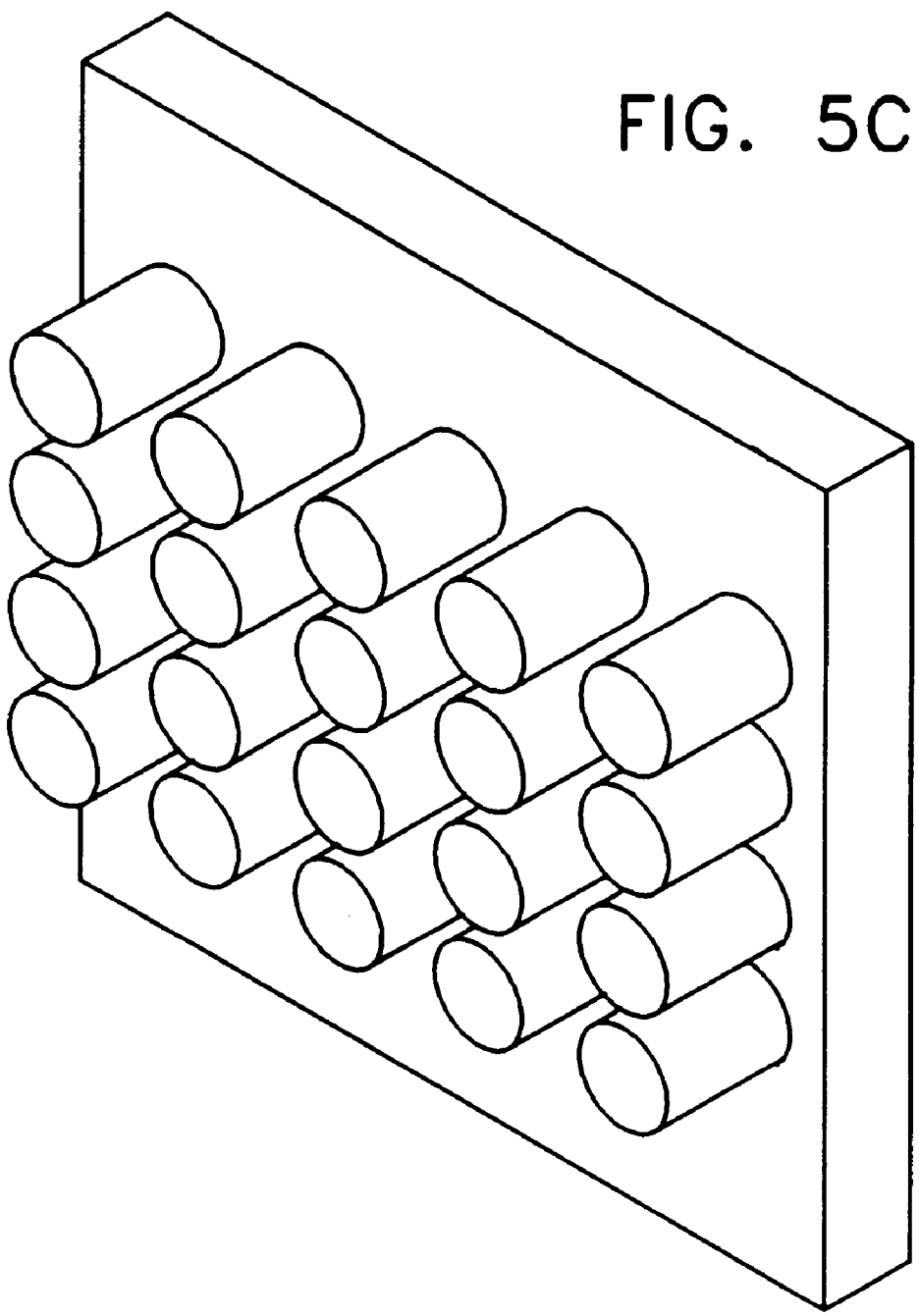
FIG. 5C shows an alternative embodiment of a multi-element probe, in accordance with a preferred embodiment of the invention.

In a further preferred embodiment of the invention, the sensing elements are formed of a conductive foam or sponge material such as silicone rubber or other conductive rubber or other elastomer impregnated with silver or other conductive material, as shown in FIG. 5C. FIG. 5C shows the sensing elements without walls 66. Elements which protrude from the substrate as shown in FIG. 5C may achieve substantial electrical isolation from one another by spacing them far enough apart so that do not contact each other in use or by coating their lateral surfaces with insulating material such as polyethylene or other soft non-conductive plastic or rubber.

For relatively short rigid or compressible elements, it has been found that reducing the size of the sensing elements such that no more than 70% (and preferably no more than 50%) of the area of the array is covered is sufficient to reduce the "cross-talk" between adjoining elements to an acceptable level.

If sufficiently good isolation is achieved between probe elements by their spacing alone, then foam or other elements without hydrogel and without walls 66 may be provided. Sensing elements such as those shown in FIG. 5C conform and mate to uneven surfaces when pressed against tissue.

Multi-element probe 62', which is preferably used for only one patient and then discarded, is preferably removably attached to a probe holder which preferably comprises a printed circuit board 80 having a plurality of contacts 82 corresponding to the contacts 74 on the back of the substrate, each PC board contact 82 being electrically connected to a corresponding contact 74 on the substrate. To facilitate alignment of the matching contacts, an alignment guide 90 is preferably provided on or adjacent to PC board 80 (FIG. 4). This guide may consist of a series of guide marks or may consist of a raised edge forming a well into or onto which the substrate is inserted. Conductors within PC board 80 connect each of the contacts to one of the pins of connector 51, which is preferably mounted on PC board 80.

Alternatively and preferably, as described below with respect to FIG. 6B, the guide may consist of two or more pins located on or near PC board 80, which fit into matching holes in probe 62'.

Alternatively as shown in FIG. 5B, the back side of the embossing of substrate 68 is used as the guide for one or more protruding elements 83 which are preferably mounted on PC board 80. Preferably a plurality of protruding elements are provided to give good alignment of the substrate with the PC board. The elements may run along the periphery of the probe and form a frame-like structure as shown in FIG. 5B or may run between the elements or may take the form of x shaped protuberances which match the shape of the embossing at the corners of the wells.

Protruding elements 83 may be formed of polycarbonate, acetate, PVC or other common inert plastic, or of a noncorrosive metal such as stainless steel.

A wire 84 is connected to each PC contact 82 and is also connected to apparatus which provides voltages to and/or measures voltages and/or impedances at the individual sensing elements 64, as described below.

In a preferred embodiment of the invention, conductive adhesive spots 86 preferably printed onto the back of the substrate are used to electrically and mechanically connect contacts 74 with their respective contacts 82. Preferably a conductive adhesive such as Pressure Sensitive Conductive Adhesive Model 102-32 (Creative Materials Inc.) is used. Alternatively, the adhesive used for printing the contacts/feed-throughs is a conducting adhesive and adhesive spots 86 may be omitted. Alternatively, pins, which protrude from the surface of PC board 80 and are connected to wires 84 pierce the substrate (which may be pre-bored) and contact the gel or hydrogel in the wells. A pin extending from the substrate may also be inserted into a matching socket in the PC board to form the electrical connection between the sensing element and the PC board. Alternatively, the entire back side of the substrate can be adhered to the printed circuit board surface using an anisotropically conductive thin film adhesive which has a high conductivity between contacts 74 and 82 and which has a low conductivity resulting in preferably many times higher resistance between adjoining contacts than between matching contacts, in practice at least one hundred times different. An example of such adhesive is tape NO. 3707 by MMM Corporation, Minneapolis Minn. However, due to the difficulty of applying such material without trapped air bubbles, it may be preferably to apply adhesive only to the contacts themselves. In practice a release liner of polyethylene, mylar or paper with a non-stick surface on one side is provided on the lower side of the adhesive sheet. This liner protects the adhesive layer prior to connection of the disposable multi-element probe to the probe holder and is removed prior to the connection of the probe to the holder.

Preferably, the impedance between contacts 82 and skin side of the conducting material in the wells should be less than 100 ohms at 1 kHz and less than 400 ohms at 10 Hz.

Impedance between any pair of contacts 82, with the multi-element probe mounted should preferably be greater than 10 kohm at 1 kHz or 100 kohm at 10 Hz.

Another suitable material for producing substrates is TYVEX (DuPont) substrate which is made from a tough woven polyolefin material available in various thicknesses and porosities. If such material having a suitable porosity is used, contacts 72 and 74 and feed-through 76 can be formed by a single printing operation with conductive ink on one side of the TYVEX sheet. Due to the porosity of the TYVEX, the inks will penetrate to the other side of the TYVEX and form both contacts and feed-through in one operation.

For probe 62 in the embodiment of FIG. 3A, substrate 68 is replaced by a relatively rigid PC board which includes conducting wires to attach each of electrical contacts 72 to one of the pins of connector 51 (FIG. 3A) and the rest of the connecting structure of FIG. 5A may be omitted. It should be noted that the choice of using the structure of FIGS. 3A or 3B (i.e., probes 62 or 62') is an economic one depending on the cost of manufacture of the probes. While probe 62 is structurally simpler, the disposable portion of probe 62' is believed to be less expensive to manufacture in large quantities. Since it is envisioned that the probes will be used in large quantities and will preferably not be reused, one or the other may be preferable.

The other side of the probe is also protected by a cover plate 88 (FIGS. 5A and 5B) which is attached using any bio-compatible adhesive to the outer edges of dividers 66 (FIG. 5A) and/or to the hydrogel, which is preferably moderately tacky. In one preferred embodiment of the invention, the inner surface of the cover plate 88 is provided with an electrically conductive layer so that the impedance of each sensing element from the outer surface of the hydrogel (or conductive gel) to contact 82, can be measured using an external source. In addition, if a known impedance is connected between the conductive layer and a reference point or a source of voltage, the sensing elements can be tested in a measurement mode similar to that in which they will finally be used.

Alternatively, a film RC circuit or circuits may be printed on the inner surface of plate 88 to simulate an actual impedance imaging situation. Alternatively, plate 88 may be provided with contacts at each sensing location, and circuitry which may simulate a plurality of actual impedance imaging situations. Such circuitry may include external or integral logic such as programmable logic arrays and may be configurable using an external computer interface. The simulation may provide a distinct RC circuit for each sensing element or may provide a sequence of different circuits to each sensing element to simulate the actual range of measurements to be performed using the probe.

FIG. 5B shows a preferred embodiment of cover sheet 88 (indicated on the drawing as 88') and its mode of attachment to both the multi-element sensor and the PC board. In this embodiment a multi-element probe 62" is optionally further attached to PC board 80 by an adhesive frame 210 which may be conductive or non-conductive, and which assists in preventing entry of water or gel under sensor 62". Sensor 62" is preferably further aligned to PC board 80 by one or more holes 222 with one or more pins 204, which are permanently attached to PC board 80 or to a surface adjacent to PC board 80. While pin 204 is shown as being round, using rectangular, triangular, hexagonal pyramidical or other shapes provides additional alignment of the sensor. In general the upper portion of the pin should be curved for improved electrical contact as described below.

The upper exposed surface of pin 204 is conductive, preferably curved and is preferably connected to a signal reference source by a conductor 202 in PC board 80. Cover sheet 88' is made of a single integral sheet of easily deformable polyethylene, Mylar or other suitable plastic. Cover sheet 88' is preferably removably attached to the upper side of multi-element probe 62" by a continuous frame of adhesive 225, which need not be conductive, but which seals around a lip where cover 88' contacts probe 62" to protect the quality and sterility of array 230 and to maintain the moisture content of any medium filling wells 70. Cover 88' is coated on the side facing probe 62" with a conductive layer 231, such as any of the various metallic coatings, for example, aluminum or the thin film coating described above.

Cover 88' is preferably formed after conductive coating, by embossing, vacuforming or other means, to have depressions 233 in the cover located over corresponding wells 70. The depressions are approximately centered on the center of the wells and held a small distance "δ1" above the surface of the hydrogel or gel, by means of relatively high sidewalls 226 which are formed at the same time as depressions 233. Furthermore, the surface of cover 88' preferably has a concave shape to match the rounded conductive contact surface of pin 204, from which it is held at a distance "δ2". Distances δ1 and δ2 are selected to minimize unintended physical contact between the conductive inner surface of the cover, the contacts in the wells and pin 204, for example, during storage and handling prior to use, which might cause corrosion over time due to electrochemical processes.

Distances δ1 and δ2 are also preferably selected so that application of a nominal force (preferably about one kilogram) against a flat outer surface 232 of cover 88', such as by a weighted flat plate, will establish contact between the inner coating 231 and the upper surface of pin 204 and with the sensing elements or the gel in the wells.

By establishing this contact, the conductive inner surface 231 is connected, on the one hand to signals source contact 202 and with each sensing element. If the coating is a conductor, the sensing elements are all excited by the signal on line 202; if it is a thin film circuit, the contact is via the thin film circuit. In either event, if line 202 is excited by a signal, the signal will be transmitted to each of the sensing elements, either directly, or via a known impedance.

In either case, the multi-element array can be tested by the system and any residual impedance noted and corrected when the probe is used for imaging. If the residual impedance of a given sensing element is out of a predetermined specification, or is too large to be compensated for, the multi-element probe will be rejected. Furthermore, the computer may be so configured that imaging may only take place after determination of the contact impedance of the sensing elements or at least of verification that the probe impedances are within a predetermined specification.

While pin 204 is shown as being higher than the top of the wells, the pin may be at the same height as the wells, or even below the wells with the cover being shaped to provide a suitable distance "δ2" as described above.

In an alternative embodiment of the invention, the contact surface corresponding to pin 204 is printed on or attached to the surface holding the sensing elements, with contact to the PC board being via a through contact in substrate 68, as for the sensing elements.

In yet another embodiment of the invention, the conductive contact surface associated with pin 204 is on the surface holding the sensing elements adjacent to pin 204. Pin 204 supports this surface and contacts the contact surface via one, or preferably a plurality of through contacts. Pin 204 is designed to match the contour of the contact surface and preferably, by such matching, to provide additional alignment of the probe on the PC board.

To avoid drying out of the Gel or other potential hazards of limited shelf life, the quality of any of the aforementioned versions of the disposable electrode arrays can be assured by incorporating an identification code, preferably including manufacturer and serial number information and date of manufacture. In a preferred embodiment, the information is coded in a bar code printed on each disposable probe, which is packaged together with at least one other such probe (typically 5–50 probes) in the same packet, which also has the same bar code. A bar code reader, interfaced with the system computer, reads the manufacturing information on the packet and each probe, checking for date and compliance and permitting recording only for a number of patients equal to the number of probes in the packet.

In a preferred embodiment of the invention a bar code may be placed on the individual disposable electrode arrays which can be read by a bar code reader installed in or under the PC board, for example near reference numeral 83 of FIG. 5B.

While the invention has been described in conjunction with the preferred embodiment thereof, namely a generally flat, somewhat flexible structure, suitable for general use and for breast screening, other shapes, such as concave structures (e.g., brassiere cups) or the like may be preferable, and in general the shape and configuration of the detectors will depend on the actual area of the body to be measured. For example cylindrical arrays can be useful in certain situations, for example in intra-rectal examinations of the prostate or colon or inside vessels. In this context, a probe according to the invention is also useful for measurements inside the body, for example gynecological measurements or measurements in the mouth, where the probe is inserted into a body cavity and contacts the lining of the cavity, and probes having shapes which correspond either flexibly or rigidly to the surface being measured can be used. For example, a multi-element probe in accordance with the invention may be incorporated into or attached to a laparoscopic or endoscopic probe.

Furthermore, sterilized probes can be used in invasive procedures in which the probe is placed against tissue exposed by incision. In this context, the term "skin" or "tissue surface" as used herein includes such cavity lining or exposed tissue surface.

In a preferred embodiment of the invention, PC board 80 and as many elements as possible of probe 62' (or the board of probe 62) are made of transparent or translucent material, so as to provide at least some visibility of the underlying tissue during placement of probe 62. Those elements of the probe and conductors in the PC board, to the extent that they are opaque should be made as small as practical to provide the largest possible view to a technician or clinician to aid in placement of the probe. Furthermore, probe 62 is slidably displaceable when used with the above-mentioned conductive gel to permit moderate lateral adjustment of the probe position, to aid in placement, to ensure good contact between each element and the tissue surface to be measured, and to enable the user to rapidly verify whether detected abnormalities are artifacts due to poor contact or are genuine objects, since artifacts remain stationary or disappear entirely when the probe is moved while genuine objects just move in a direction opposite to the direction of movement of the probe.

The general shape and size of the multi-element probe and the size of the conductive sensing elements will depend on the size of the area to be measured and on the desired resolution of the measurement. Probe matrix sizes of greater than 64×64 elements are envisioned for viewing large areas and probes which are as small as 2×8 elements can be useful for measuring small areas. Element size is preferably between 2 mm square and 8 mm square; however, larger sizes and especially smaller sizes can be useful under certain circumstances. For the breast probe 62 described above, 24×32 to 32×40 elements appear to be preferred matrix sizes.

Figure 6A:
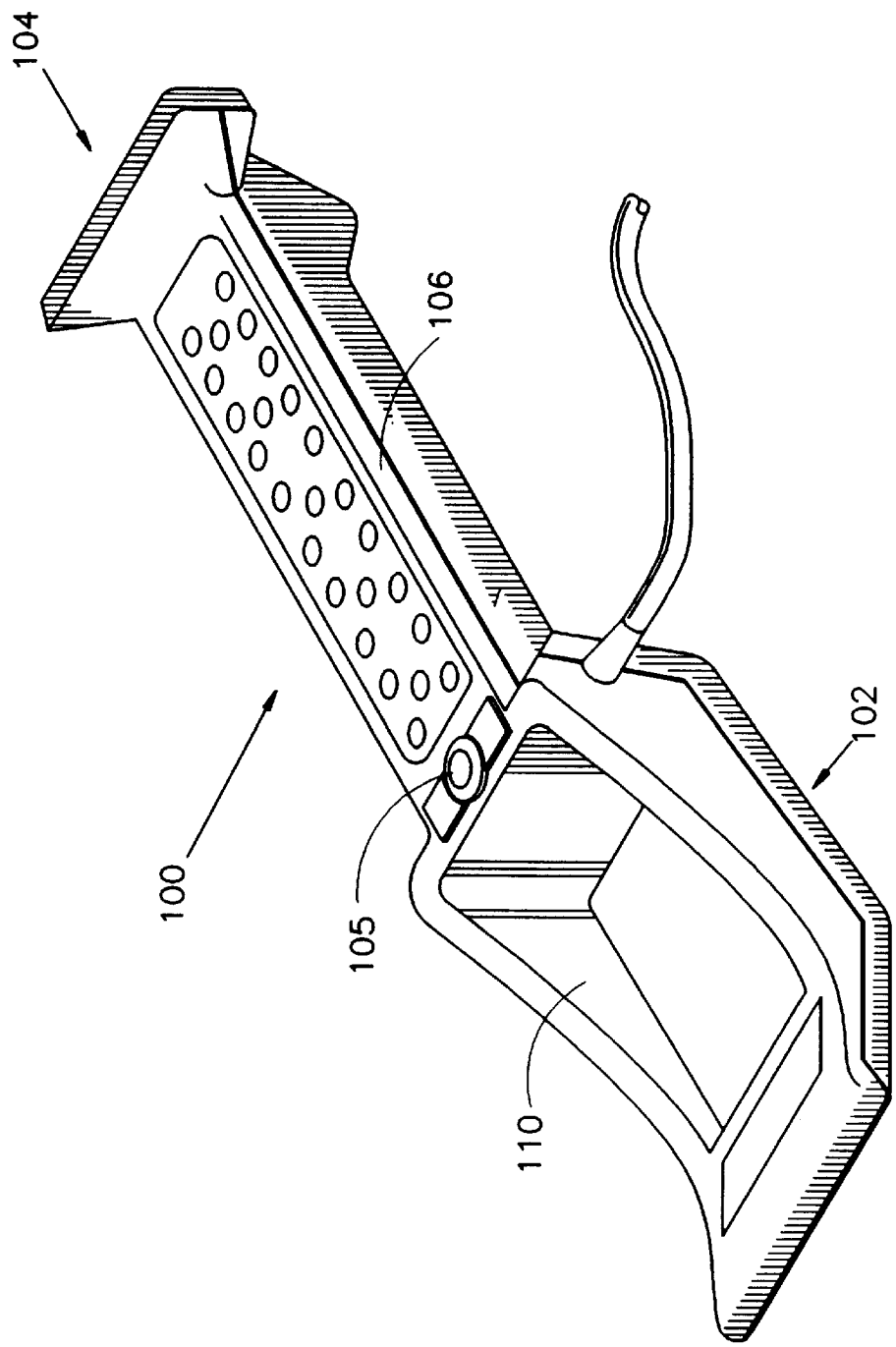
FIG. 6A is a perspective view of a hand held probe in accordance with a preferred embodiment of the invention.

FIG. 6A shows a perspective view of a hand held probe 100 in accordance with a preferred embodiment of the invention. Probe 100 preferably comprises two probe heads, a larger head 102 and a zoom sensor head 104. A handle 106 connects the sensor heads, houses switching electronics and provides means for holding and positioning the probes. Handle 106 also optionally incorporates a digital pointing device 105 such as a trackball, pressure sensitive button or other such joystick device. Incorporation of a pointing device on the probe enables the operator to control the system and input positional information while keeping both hands on either the probe or patient. As described below, the digital pointing device can be used to indicate the position on the patient's body at which the image is taken.

FIG. 6B shows a partially expanded bottom view of probe 100 of FIG. 6A, in accordance with a preferred embodiment of the invention. Where applicable, like parts of the probes throughout this disclosure are similarly numbered. Starting from the bottom of FIG. 6B, the top half of a housing 108A has a well 110 formed therein. A clear plastic window 112 is attached to the edge of well 110, and a printed circuit on a relatively transparent substrate, such as Kapton, designated by reference 80' (to show its similarity to the corresponding unprimed element of FIG. 5) is placed on window 112. A flexible print cable 114 connects the contacts on printed circuit 62' to acquisition electronics 116. A cable 118 connects the acquisition electronics to the computer. A second similarly constructed, but much smaller zoom sensor probe head is attached to the other end of probe 100. Either of the larger or smaller heads may be used for imaging.

A lower half of housing 108B, encloses electronics 116 and print 80', whose face containing a series of contacts 82', is available through an opening 120 formed in the lower housing half 108B. A mounting frame 122 having two alignment pins 124 holds print 80' in place. Mounting and connecting screws or other means have been omitted for simplification.

A disposable multi-element probe 62', similar to that of FIG. 5 is preferably mounted on the mounting frame to complete the probe.

FIG. 7A is a perspective view of a fingertip probe 130 in accordance with a preferred embodiment of the invention as mounted on the finger 132 of a user. Probe 130 may be separate from or an integral part of a disposable glove, such as those normally used for internal examinations or external palpation. The fingertip probe is especially useful for localizing malignant tumors or investigating palpable masses during surgery or during internal examinations. For example, during removal of a tumor, it is sometimes difficult to determine the exact location or extent of a tumor. With the local impedance map provided by the fingertip probe 130 and the simultaneous tactile information about the issue contacted by the probe, the tumor can be located and its extent determined during surgery. In a like fashion, palpable lumps detected during physical breast (or other) examination can be routinely checked for impedance abnormality.

Figure 7B:
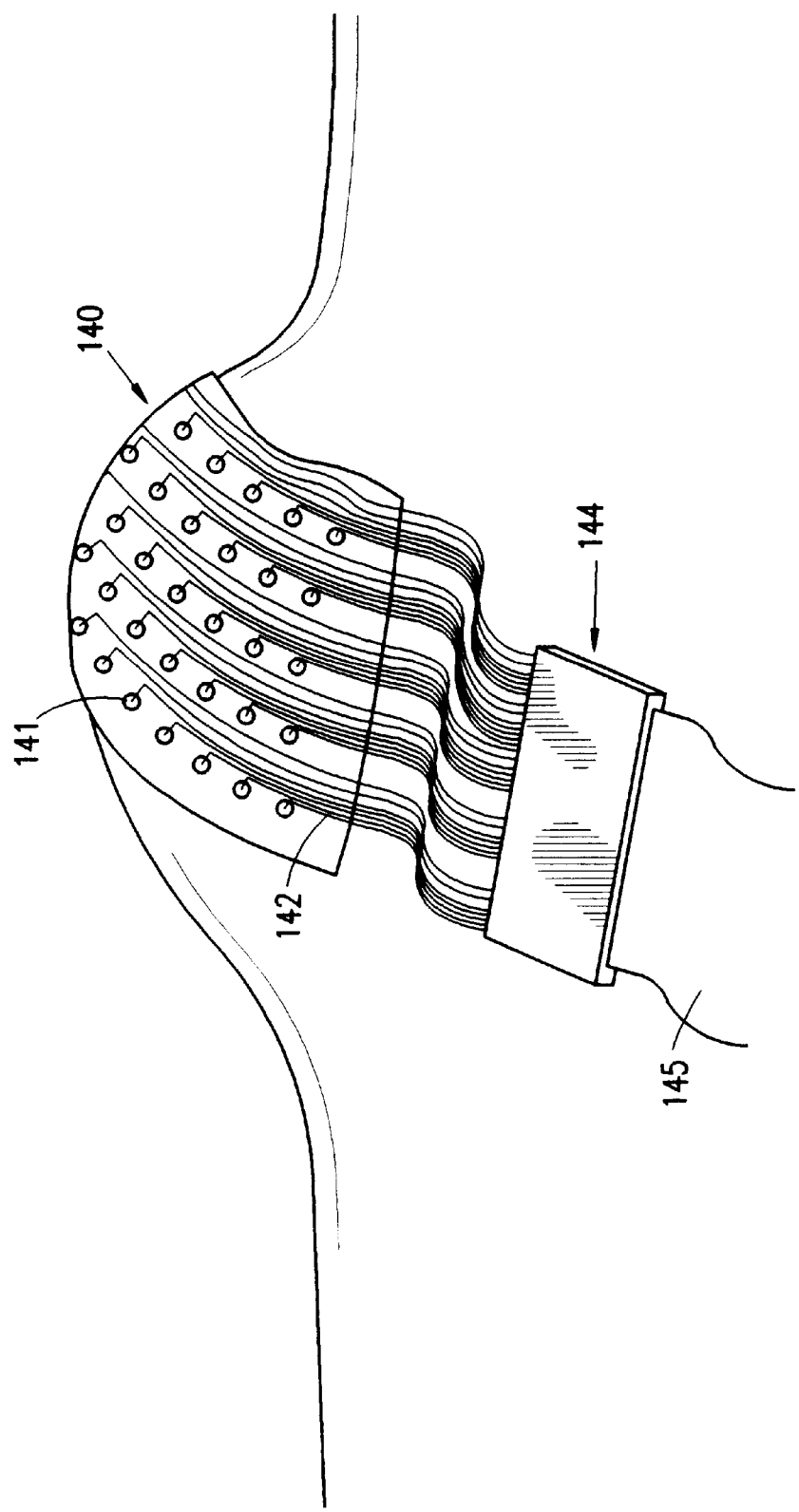
FIG. 7B shows a conformal multi-element probe.

FIG. 7B shows a flexible probe array 140 which is shown as conforming to a breast being imaged. Probe array 140 comprises a plurality of sensing elements 141 which contact the tissue surface which are formed on a flexible substrate. Also formed on the flexible substrate are a plurality of printed conductors 142 which electrically connect the individual sensing elements 141 to conductive pads on the edge of the substrate. A cable connector 144 and cable 145 provide the final connection link from the sensing elements to a measurement apparatus. Alternatively, the flexible array may take a concave or convex shape such as a cup (similar in shape to a bra cup) which fits over and contacts the breast.

The flexible substrate is made of any thin inert flexible plastic or rubber, such as those mentioned above with respect to FIG. 5A. Array 140 is sufficiently pliant that, with the assistance of viscous gel or conductive adhesive, the sensor pads are held in intimate contact with the skin or other surface, conforming to its shape.

Figure 8:
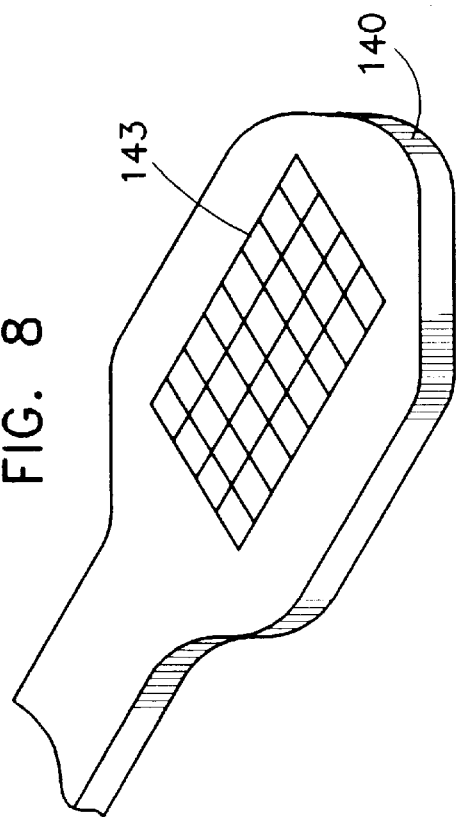
FIG. 8 shows an intra-operative probe used determining the position of an abnormality in accordance with a preferred embodiment of the invention.

FIG. 8 shows an intra-operative paddle type probe 140 used, in a similar manner as probe 130, for determining the position of an abnormality in accordance with a preferred embodiment of the invention. This probe generally includes an integral sensing array 143 on one side of the paddle. Preferably, the paddle is made of substantially transparent material so that the physical position of the array may be determined and compared with the impedance map.

Figure 9:
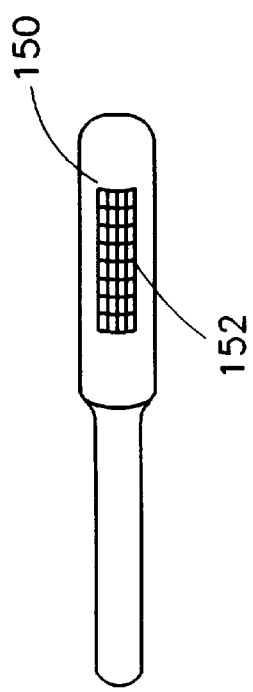
FIG. 9 shows a laparoscopic probe in accordance with a preferred embodiment of the invention.

FIG. 9 shows a laparoscopic probe 150 in accordance with a preferred embodiment of the invention. Probe 150 may have a disposable sensing array 152 mounted on its side or the sensing array may be integral with probe 150, which is disposable or sterilizable.

Multi-element probes, such as those shown in FIGS. 7, 8 and 9, are preferably disposable or sterilizable as they are generally are used inside the patients body in the presence of body fluids. In such situations, there is generally no need or desire for a conductive gel in addition to the probes themselves. Generally, printed sensing elements, such as those printed with silver-silver chloride ink, or sensing elements formed of conductive silicone, hydrogel or of a conductive sponge may be used. While in general it is desirable that the sensing elements on these multi-element probes be separated by physical separators 66 (as shown in FIG. 5), under some circumstances the physical distance between the elements is sufficient and the separators may be omitted.

When performing a needle biopsy, a physician generally relies on a number of indicators to guide the needle to the suspect region of the body. These may include tactile feel, X-Ray or ultrasound studies or other external indicators. While such indicators generally give a reasonable probability that the needle will, in fact take a sample from the correct place in the body, many clinicians do not rely on needle biopsies because they may miss the tumor.

Figure 10:
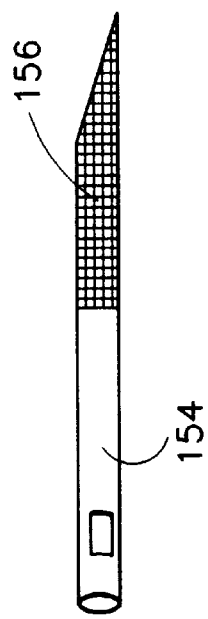
FIG. 10 shows a biopsy needle in accordance with a preferred embodiment of the invention.

FIG. 10 shows a biopsy needle 154, in accordance with a preferred embodiment of the invention, which is used to improve the accuracy of placement of the needle. Biopsy needle 154 includes a series of sensing elements 156 spaced along the length of the probe. Leads (not shown) from each of these elements bring signals from the elements to a detection and computing system such as that described below. Elements 156 may be continuous around the circumference, in which case they indicate which portion of the needle is within the tumor to be biopsied. Alternatively, the electrodes may be circumferentially segmented (a lead being provided for each segment) so that information as to the direction of the tumor from the needle may be derived when the needle is not within the tumor. Such an impedance sensing biopsy needle can be used, under guidance by palpation, ultrasound, x-ray mammography or other image from other image modalities (preferably including impedance imaging as described herein), taken during the biopsy or prior to the biopsy to improve the accuracy of placement of the needle. In particular, the impedance image from the needle may be combined with the other images in a display. While this aspect of the invention has been described using a biopsy needle, this aspect of the invention is also applicable to positioning of any elongate object such as an other needle (such as a localizing needle), an endoscopic probe or a catheter.

Returning now to FIGS. 1–3 and referring additionally to FIGS. 11–14, a number of applications of multi-element probes are shown. It should be understood that, while some of these applications may require probes in accordance with the invention, others of the applications may also be performed using other types of impedance probes.

Figure 11A:
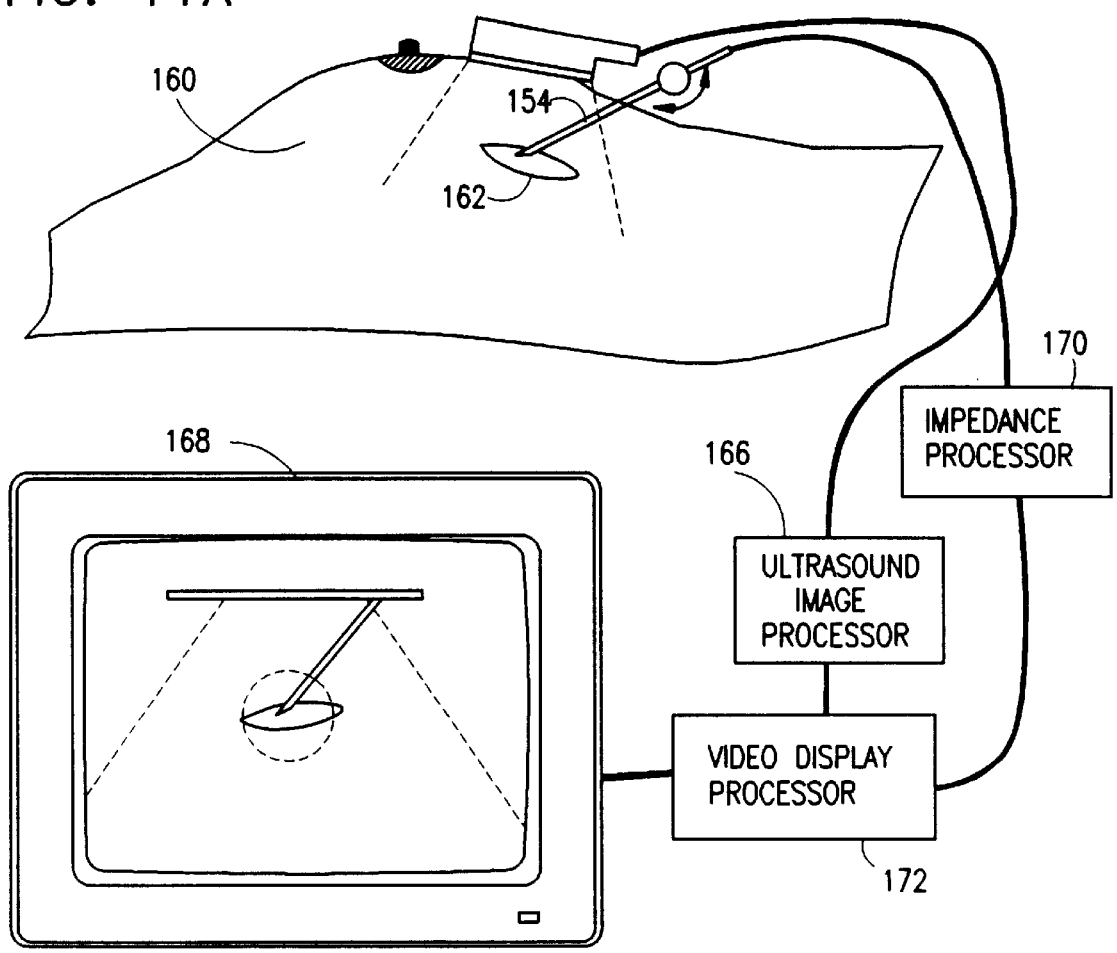
FIG. 11A illustrates a method of using the biopsy needle of FIG. 10, in accordance with a preferred embodiment of the invention.

FIG. 11A shows the use of the biopsy needle in FIG. 10 together with an optional ultrasound imaging head in performing a biopsy. A breast 160 having a suspected cyst or tumor 162 is to be biopsied by needle 154. An ultrasound head 164 images the breast and the ultrasound image, after processing by an ultrasound processor 166 of standard design is shown on a video display 168. Of course, the ultrasound image will show the biopsy needle. The impedance readings from probe 154 are processed by an impedance processor 170 and are overlaid on the ultrasound image of the biopsy needle in the display by a video display processor 172.

Figure 11B:
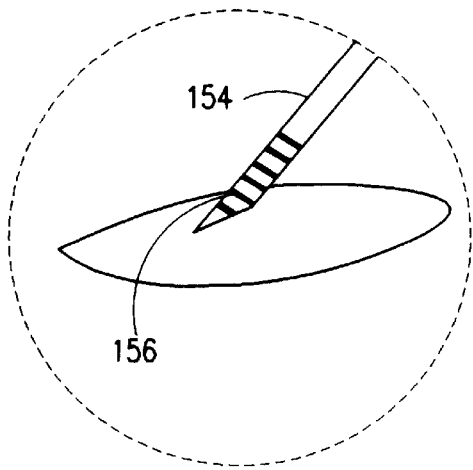
FIG. 11B illustrates a portion of a display used in conjunction with the method of FIG. 11A.
Figure 11C:
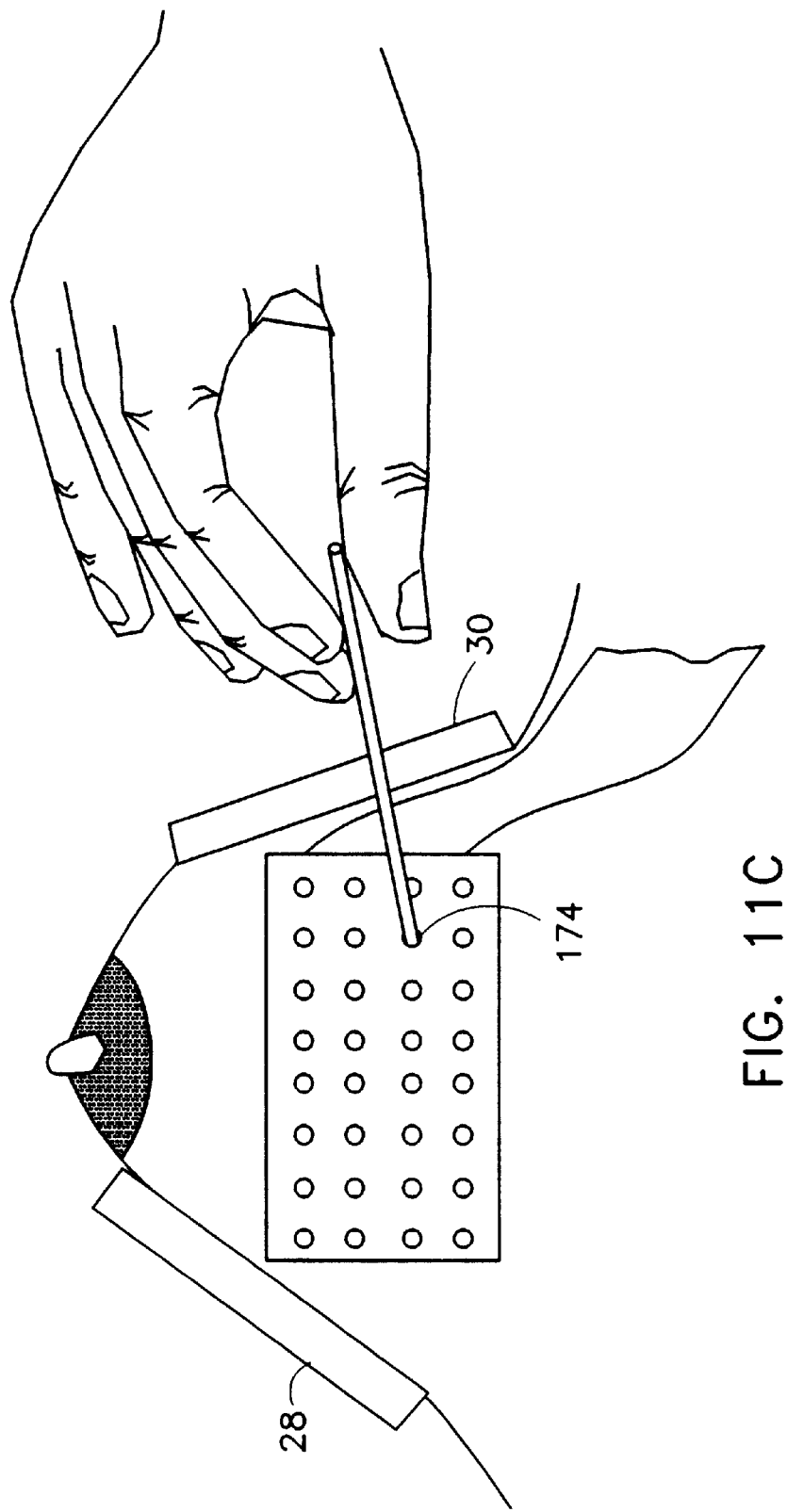
FIG. 11C shows a biopsy guiding system in accordance with a preferred embodiment of the invention.

In one display mode, the portions, as shown in FIG. 11B of the needle which are within the tumor or cyst and which measure a different impedance from those outside the tumor, will be shown in a distinctive color to indicate the portion of the needle within the tumor or cyst. In a second display mode, the impedance measured will be indicated by a range of colors. In yet a third embodiment of the invention, in which circumferentially segmented sensing elements are employed, the impedance processor will calculate radial direction of the tumor from the needle and will display this information, for example, in the form of an arrow on the display.

The image sensing biopsy needle can also be used with one or more imaging arrays (28, 30) such as those shown in FIG. 6 or FIG. 3B to impedance image the region to be biopsied during the biopsy procedure. Alternatively, at least one of the arrays can be an imaging array of the non-impedance type. In one preferred embodiment, shown in FIG. 11C, the needle is inserted through an aperture (or one of a plurality of apertures) 174 in a multi-element probe which is imaging the region. The region may, optionally, be simultaneously viewed from a different angle (for example at 90° from the probe with the aperture) with an other impedance imaging probe. In the case that both arrays 28 and 30 are impedance imaging arrays, the biopsy needle or other elongate object can either have impedance sensing or not, and the two images help direct it to the region. The probe with one or more apertures is sterile and preferably disposable. This biopsy method is shown, very schematically, in FIG. 11C.

In an alternative preferred embodiment of the invention, only the perforated plate through which the needle or elongate object is passed is an imaging array. In this case the array through which the needle passes give a two dimensional placement of the impedance abnormality while an imaging or non-imaging impedance sensor on the needle gives an indication of when the needle has reached the region of impedance abnormality, as described above.

Figure 11D:
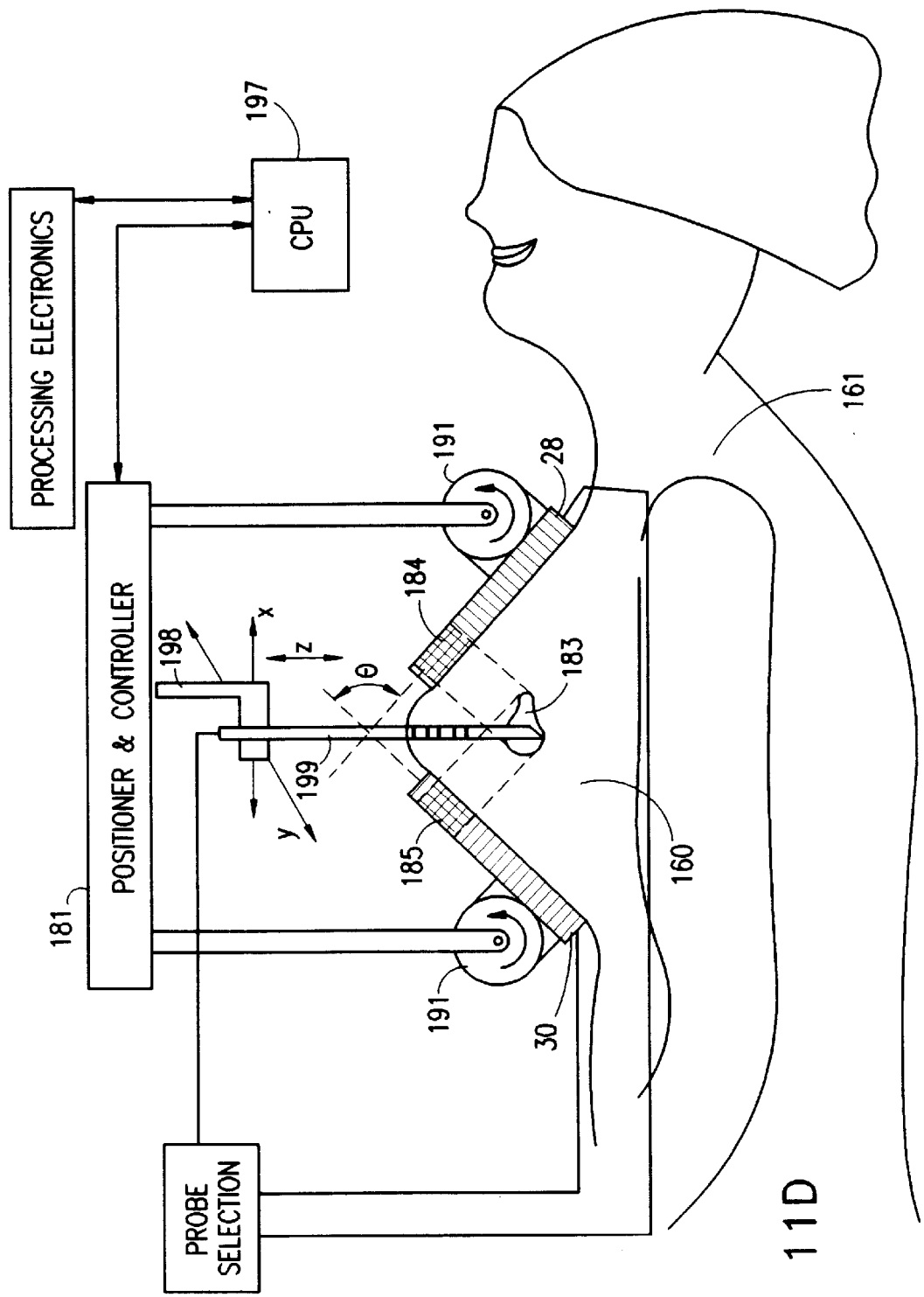
FIG. 11D shows a frontal biopsy guiding system in accordance with a preferred embodiment of the invention.
Figure 11E:
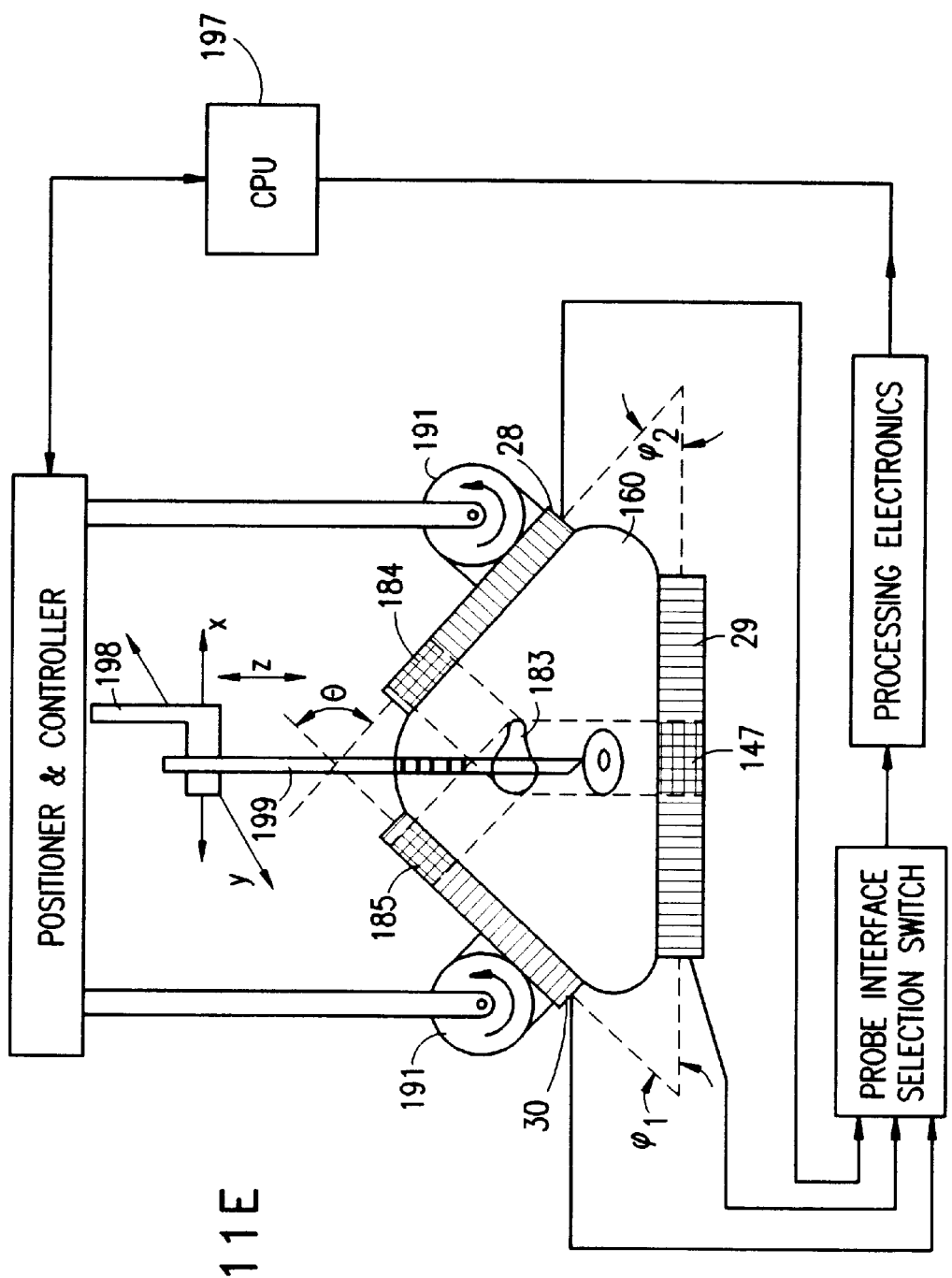
FIG. 11E shows a lateral biopsy guiding system in accordance with a preferred embodiment of the invention.

Alternative guiding systems for frontal and lateral breast biopsy or for guiding an elongate element to a desired impedance region of the body are shown in Figs. 11D and 11E, respectively.

FIG. 11D shows a system for in which two relatively large plate multi-element probes 28, 30 are placed on opposite sides of the desired tissue, shown as a breast 160 of a prone patient 161. Sensor array probes 28 and 30 are held in position by positional controller 181 via rotatable mounts 191. A mount 198 positions a biopsy needle 199 within the opening between probe arrays 28 and 30, and is operative to adjust its height. A suspicious region 183 which is located at positions 184 and 185 on arrays 28 and 30 respectively as described herein, which information is supplied to a CPU 197, which determines the position of the suspicious region for controller 181. The controller then inserts the needle into the suspicious region, for example, to take the biopsy. Biopsy needle 199 is preferably of the type shown in FIG. 10 to further aid in positioning of the needle. As indicated above, this is not required for some embodiments of the invention.

Alternatively, biopsy needle 199 may be inserted through holes formed between the elements of probes 28 and/or 30 as described above. Furthermore, while automatic insertion of the biopsy needle is shown in FIG. 11D, manual insertion and guidance based on impedance images provided by the probes is also feasible.

FIG. 11E shows a system similar to that of FIG. 11D in which the imaging and biopsy needle insertion is from the side of the breast, rather than from the front. Operation of the method is identical to that of FIG. 11D, except that an additional probe 29 may be provided for further localization of suspicious region 183. Alternatively, one or two of the probes may be substituted by plates of inert material for holding and positioning the breast.

It should be noted that while the breast has been used for illustrative purposes in FIGS. 11A through 11E, the method described is applicable to other areas of the body, with necessary changes due to the particular physiology being imaged.

It should be understood that one or more of the elements on the needle may themselves be electrified to cause them to "light-up" on the image. This electrification may be AC or DC may be the same or different from the primary image stimulus, may have a single frequency or a complex form and may be applied in a continuous or pulsed mode. If one or more of the sensing elements is used in this manner, said elements are preferably alternatively used to apply an electrification signal and to function as sensors, i.e., to sense signals from the primary stimulus.

Figure 12:
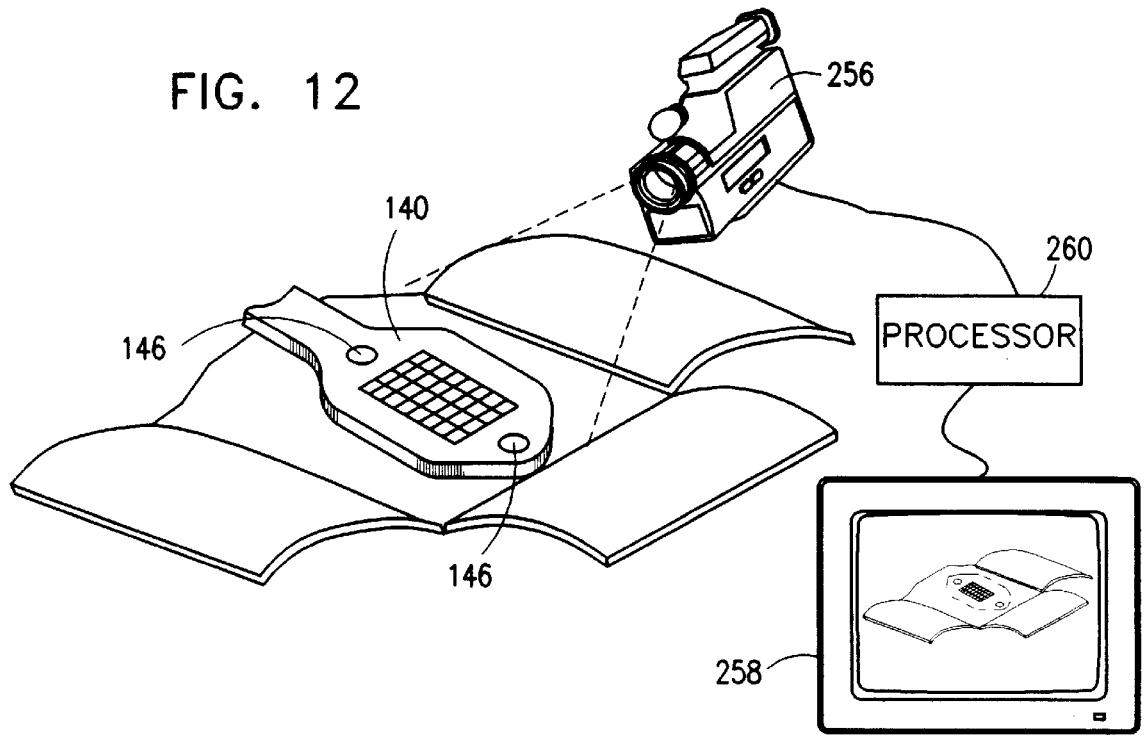
FIG. 12 shows, very schematically, the inter-operative probe of FIG. 8 combined with a video camera use to more effectively correlate an impedance measurement with placement of the probe.

FIG. 12 shows, very schematically, the intra-operative probe of FIG. 8 combined with a video camera 256 to more effectively correlate the impedance measurement with the placement of the probe on the body. An intra-operative probe 140 preferably having a number of optically visible fiduciary marks 146 is placed on the suspect lesion or tissue. A video camera 256 sequentially views the area without the probe and the same area with the probe in place and displays a composite image on a video display 258 after processing by a processor 260. Processor 260 receives the impedance data from probe 140, determines the positions of the fiduciary marks from the video image and superimposes the impedance image on the video image, with or without the probe, which is displayed on display 258.

Figure 13:
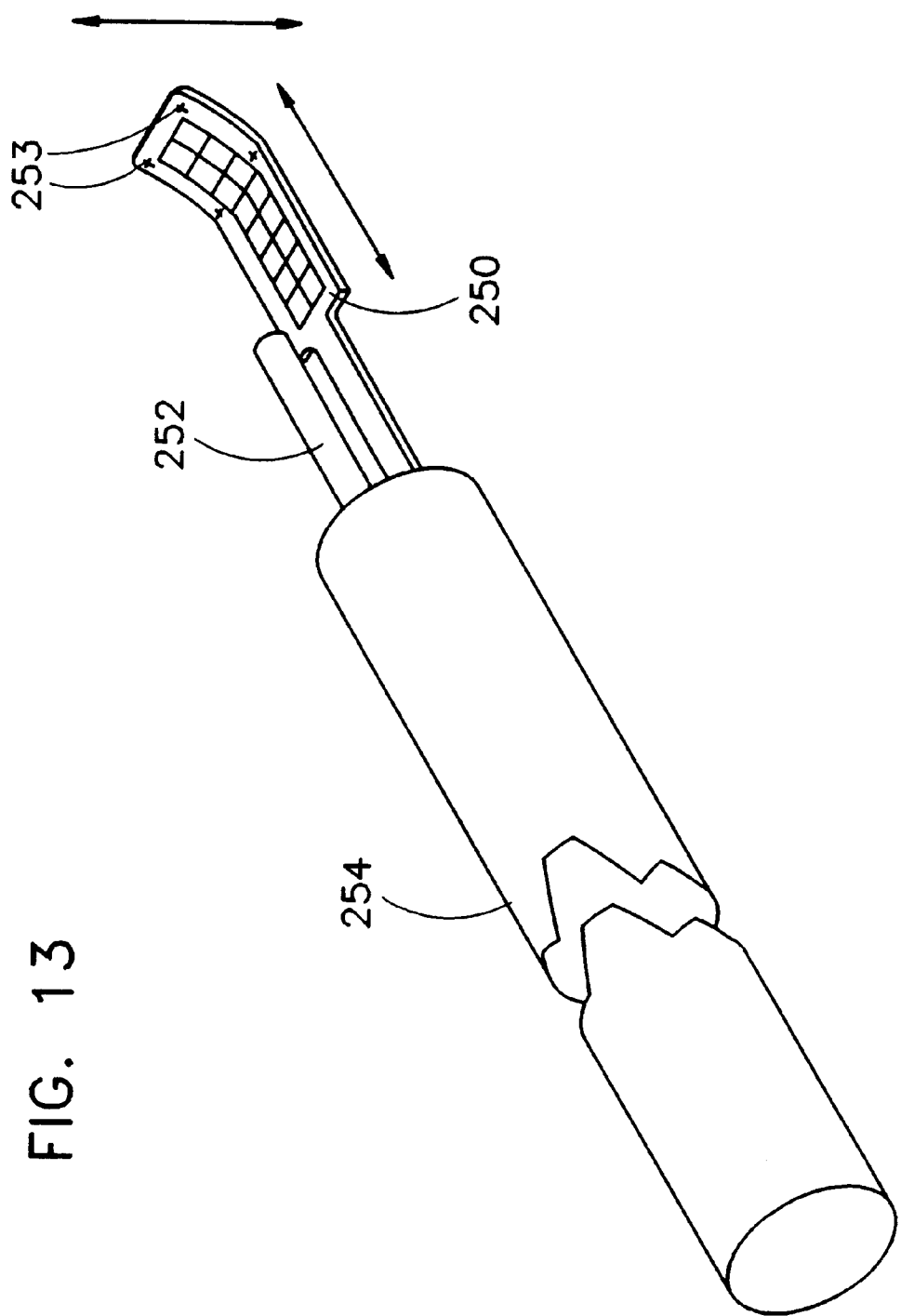
FIG. 13 illustrates a laparoscopic probe according to the invention used in conjunction with a fiber-optic illuminator-imager.

FIG. 13 shows a laparoscopic or endoscopic probe 250 used in conjunction with a fiber-optic illuminator/imager 252. In this embodiment, the laparoscopic impedance probe, which is formed on a flexible, preferably extendible paddle, is viewed by the illuminator/imager which is preferably a video imager, which is well known in the art. Probe 250 can be either round or flat, depending on the region to be imaged. When the imager views a suspicious lesion or tissue, probe 250 is extended to determine the impedance properties of the lesion. The combination of probe 250 and imager 252 may be incorporated in a catheter 254 or other invasive element appropriate to the region of the body being investigated.

Optically visible fiduciary marks 253 on probe 250 are preferably used to determine the position of probe 250 within the video image of the tissue seen by fiber-optic illuminator/imager 252, in a manner similar to that discussed above with respect to FIG. 12.

In a preferred embodiment of a system using any of the biopsy needle, intra-operative probe, finger tip probe or other embodiments described above, an audible sound proportional to an impedance parameter measured by the needle or other sensor in or on the body is generated by the system computer. This feature may be useful in situations where the probe is placed in locations which are difficult to access visually, such as suspected lesions during surgery. Such an audible sound could include any kind of sound, such as a tone whose frequency is proportional to the measured parameter or similar use of beeps, clicks, musical notes, simulated voice or the like. This feature can also be used for non-surgical procedures such as rectal, vaginal or oral examinations, or other examinations.

Figure 16:
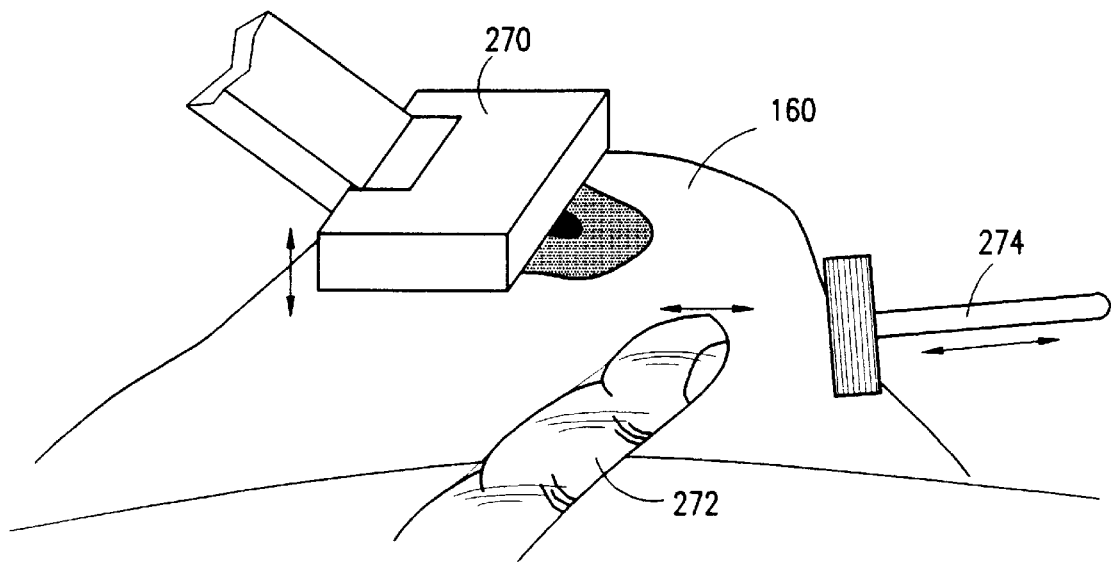
FIG. 16 illustrates a method useful for verifying a detected local impedance deviation as being non-artifactal and for estimating the deviation.

FIG. 16 shows methods useful for estimating the depth of a lesion and also for determining if a image contains a true lesion or an artifact.

A breast or other region 160 is imaged by a probe 270, for example, the probe of FIGS. 1–3 or FIGS. 6A and 6B. The depth of a local impedance deviation can be estimated by palpating the breast or other region by a finger 272 or a plunger 274. The displacement of the local deviation on the image will be maximized when the palpation is at the same level as the lesion. It should also be understood that, where palpation causes movement of the local deviation on the impedance image, this is an indication that the deviation is "real" and not an artifact.

In a similar manner, application of variable compression to the imaging probe will result in a variation of the distance from the probe to deviation under the probe. This distance variation will cause a corresponding variation in the size and intensity of the deviation, thus helping to verify that the deviation is not artifactal.

Alternatively or additionally, the probe can be moved along the surface of the tissue without moving the tissue. In this case, surface effects will have a tendency to either disappear or to move with the probe (remain stationary in the image) while real anomalies will move, on the image, in the opposite direction from the movement of the probe.

Alternatively or additionally, the probe and the tissue can be moved together without moving the underlying structure (such as the bones). Tissue lesions will remain relatively stationary in the image while bone artifacts will move in the opposite direction.

In operation, a system according to the present invention measures impedance between the individual sensing elements and some reference point (typically the signal source point) at some other place on the body. Generally, in order to produce an interpretable impedance image, the sensing elements in the multi-element probe should detect distortions in the electric field lines due solely to the presence of a local impedance difference between embedded tissue of one type (for example, a tumor) and surrounding tissue of another type (for example, normal adipose tissue).

To avoid distortion in the field lines, the reference point is typically placed far from the sensor array, all sensing elements are all at ground or virtual ground, and the current drawn by the elements is measured. Since the probe is at ground (an equipotential) the electric field lines (and the current collected by the elements) are perpendicular to the surface of the multi-element probe. In principle, if there are no variations of impedance below the probe, each element measures the integrated impedance below the element. This first order assumption is used in the determination of the position and/or severity of a tumor, cyst or lesion. It is clear, however, that the multi-element probe covers only a portion of even the organ which is being imaged. The area outside the area of the probe is not at ground potential, causing the field lines to bend out at the periphery of the probe, biasing the edge of the impedance image.

To reduce this effect, a conductive "guard ring" is provided around the edge of the imaged area to draw in and straighten the field lines at the edge of the imaged area. This guard ring, if one is desired, can consist of merely ignoring the, presumably distorted, currents drawn by the elements at (or near) the edge of the probe and ignoring the measurements made by these elements. In general, while the use of a guard ring reduces the edge effect at the edge of the field, it is still generally necessary to determine values for comparison or determination of polychromic values near the ring based only on pixels near the ring and not on the image as a whole.

Furthermore, to possibly reduce the baseline impedance contributed to the local impedance image by tissue between the remote signal source and the region near the probe, an additional reference electrode may be placed on the patient's body relatively near the multi-element probe. For example, if the source is placed at the arm of the patient and the breast is imaged from the front, a reference electrode for sensing a reference voltage can be placed at the front of the shoulder of the patient. The measured impedances are then reduced by the impedance value of the reference electrode. Alternatively, the impedance values of the elements of the multi-element probe are averaged to form a reference impedance, and the display of the impedance map is corrected for this reference impedance.

One way to substantially avoid at least some of the above-mentioned problems is to use the apparatus shown in FIGS. 1–3. As indicated above, the apparatus incorporates two probe heads 28 and 30. The breast to be imaged is placed between the probe heads and the breast is compressed by the heads (although generally to a lesser degree than in X-Ray mammography) so that the breast forms a relatively flat volume and fills the region between the probes. It should be noted that, if the current is measured at each of the sensing elements in both probes, then two somewhat different images of the same region are generated. Avoidance of the problems also results when the two multi-element probes are not parallel as described above.

It should be noted that when used on breasts, the images produced by the pair of large, flat probes of FIG. 3 have the same geometric configuration as standard mammograms. Furthermore if used in the same compression orientations, the impedance images can be directly compared to the corresponding mammograms. In one preferred embodiment of the invention, mammograms corresponding to the impedance images to be taken are digitized, using film scanning or other digitization means known in the art, and entered into the system computer. If the mammogram is already digital, such as may be provided by a digital mammogram, the image file can be transferred from the mammogram.

The mammograms and impedance images can be overlaid or otherwise combined to form a single image. Such an image could highlight those areas of the mammogram in which the impedance is particularly low or high. Such a combined image thus presents two independent readouts (impedance and radiographic density) of the same well defined anatomical region in a known geometric orientation, to facilitate interpretation, correlation with anatomy and localization.

It is well known that the resolution of objects in an impedance image is reduced with distance of the object from the probe. Thus, it is possible to estimate the distance of the object from the two probes based on the relative size of the same object on the two different probes. As indicated above, two opposing views of the breast may be taken. This would provide further localization of the object.

In one mode, the sensing elements of one probe are all electronically floating while the elements of the other probe are at a virtual ground (inputs to sensing electronics), and a remote signal source is used, as previously described. After an image is obtained from the one probe, the roles of the two probes are reversed to obtain an image from the other probe.

Alternatively, if all of the elements of one of the flat probes are electrified to the same voltage and the measuring probe is kept at virtual ground, the currents drawn from and received by the elements of both probes form a two dimensional admittance image of the region between the probes.

In a further preferred embodiment of the invention, one or a few closely spaced sensing elements on one of the probes is electrified, and the others are left floating. This would cause a beam-like flow of current from the electrified elements to the other sensing elements on the other probe. The object would disturb this flow causing impedance variations which are strongest for those elements which are in the path of the current disturbed by the object. If a number of such measurements are made with, each with a different group of electrodes being electrified, then good information regarding the position of the object can be obtained.

In practice, as indicated above, orthogonal views of the breast are taken giving additional position information.

In preferred embodiments of the invention the breast is imaged at a plurality of frequencies and both the real and imaginary parts of the impedance are calculated. The sensitivity of the detection of malignant tissue is a function of frequency, and, for a particular frequency, is a function of the impedance measure or characteristic used for imaging, for example, real part of the impedance (or admittance), imaginary part of the impedance (or admittance), absolute value of the impedance (or admittance), phase of the impedance (or admittance), the capacitance or some function of the impedance or of admittance components.

In a practical situation, an impedance measure should give the maximum contrast between a malignancy and non-malignant tissue. It is therefore desirable to determine the frequency or combination of frequencies which give maximum detectability and to determine it quickly. One method of determining the frequency is to perform swept frequency measurements and to use the frequency or combination of frequencies which results in the best contrast. Alternatively, a number of images taken at relatively close frequencies can be used. It is believed that for many purposes, at least four samples should be taken in the range between and including 100 and 400 Hz and, preferably, at least one or two additional images are taken at frequencies up to 1000 Hz.

A second method is to use a pulsed excitation and Fourier analysis to determine impedance over a range of frequencies. The optimum frequency or frequencies determined from the swept or pulsed measurement are then used in a single or multiple frequency measurement. A pulse shape which has been found useful in this regard is a bi-polar square pulse having equal positive and negative going pulses of 5–10 millisecond duration and fast rise and fall times.

A number of measures of the impedance, as described below, have been found useful for comparing different areas of the image. Generally, it is useful to display a gray scale or pseudo-color representation of the values of the impedance measure, either on a linear scale or where the square of the impedance measure is displayed. Also useful is an "absorption scale" where the value of an impedance measure, v, is displayed as:

$$d(v)=(max-1)*(exp(v*(max-1)-1))/(e-1),$$

where max is the maximum normalized value of v. Generally, the display is most useful when the measure is normalized, either by division or subtraction of the minimum or average value of the measure in the display or the estimated standard deviation or other measure of variance for the image.

Furthermore, the display may be automatically windowed to include only those values of the impedance measure actually in the image, or to include a relative window of selectable size about the average value of the impedance measure. The range of values to be displayed may also be determined using a baseline average value measured at a region remote from irregularities, i.e., remote from the nipple of the breast. Alternatively, the baseline average may be a predetermined average value as measured for a large group of patients. Alternatively, a reference region on the image may be chosen by the user to determine the baseline average to be used for windowing. While the display may show the exact measure for each pixel as is conventional, for example, in displays of nuclear medicine images, in a preferred embodiment of the invention the display is an interpolated image formed by quadratic or cubic spline interpolation of the impedance measure values. This type of display removes the annoying checkerboard effect of the relatively low resolution impedance image without any substantial loss of spatial or contrast detail.

The measures of impedance which have been found useful for comparing different areas of the image may be grouped as single frequency measures and polychromic measures.

Single frequency measures include the admittance, capacitance, conductance and phase of the admittance and its tangent. These measures may be measured at some predetermined frequency, at which the sensitivity is generally high, or at a frequency of high sensitivity determined by a preliminary swept or pulsed measurement. Cancer typically has significantly higher phase than the average surrounding tissue, with greatest difference at low frequencies such as 100 Hz, but often significant up to 5 KHz.

Polychromic impedance measures are based on measurements at more than one frequency, such as on a spectral curve based on fitting a set of capacitance (C) and conductance (G) values determined at a plurality of frequencies using linear interpolation, quadratic interpolation, cubic spline, band limited Fourier coefficients, or other methods known in the art.

One polychromic measure is a spectral width measure. For a given pixel or region of interest the value of C parameter falls (and the G parameter rises) with frequency. The spectral width of the spectrum is the width to a given percentage fall in the C value as compared to the value at some low frequency, for example 100 Hz. If the parameter does not fall by the given percentage in the measured range it is assigned an impedance measure equal to the full measured bandwidth. Similarly, the spectral width of the G-spectrum is the width to a given rise in the G-Parameter compared to the value at some low frequency, for example 100 Hz, or alternatively, the fall in G with decreasing frequency compared to the value at some high frequency, for example 3000 Hz.

A second polychromic measure is a spectral quotient in which the impedance measure is the ratio of the measured value of G or C parameters at two preset frequencies, which may be user selected, or which may be selected based on the swept or pulsed measurements described above. This measure, as all of the others may be displayed on a per-pixel basis or on the basis of a region of interest of pixels, chosen by the user.

A third type of polychromic measure is based on a Relative Difference Spectrum determination. In this measure, the capacitance or conductance for a given region of interest (or single pixel) is compared to that of a reference region over the spectrum to determine a numerical difference between the two as a function of frequency. The thus derived Relative Difference Spectrum is then analyzed. For example, a spectral width measure as described above has been found to be a useful measure of abnormalities. Normally the width is measured where the relative difference spectrum passes from positive to negative, i.e., where the C or G is equal to that of the reference region. For capacitance, this spectrum width is designated herein as the Frequency of Capacitance Crossover (FCX). This measure has been found to be especially useful in classification of tissue types as described below.

A fourth type of polychromic measure is based on a Relative Ratio Spectrum determination. This is similar to the Relative Difference Spectrum, except that the ratio of the values between the reference area and the region of interest is used. A spectral width measure can be determined for this spectrum in the same manner as for the Relative difference Spectrum. Normally, the width is measured where the ratio is 1. This width is the same as the width of Relative Difference Spectrum at the zero (cross-over) point.

A fifth type of polychromic measures are the Positive and Negative Integrated Relative Difference for Capacitance and/or Conductance abbreviated C (for capacitance) or G (for conductance) NIRD or PIRD. These values are calculated by adding up the negative (or positive) deviations of the capacitance (or conductance) values in the area of abnormality from those of a representative value (or range of values) of the capacitance (or conductance) at the various measured frequencies. This representative value or range is determined from pixel values in the image selected to exclude exceptionally high or low capacitance (or conductance) values. The same pixel may have both a C-NIRD and a C-PIRD if its capacitance deviates positively from the representative value for some subset of the frequencies and negatively from the representative value for a different subset of the frequencies. The C-NIRD, C-PIRD and G-NIRD measures have been found to be especially useful for characterizing tissue type as described below.

A sixth polychromic measure is the integrated phase. For a given pixel in the image, the phase is measured at a plurality of frequencies in a desired frequency range, typically 100 to 5000 Hz. The integrated phase is the sum of the phase over a number of frequencies, typically about 13 frequencies between 100 and 3200 Hz. Alternatively, integration may be performed using the trapezoidal rule or by integrating another functional fit to the sampled values in the desired frequency range. Cancer typically has significantly higher integrated phase. The integrated tangent of the phase is an alternative measure of this measure.

A seventh polychromic measure is the integrated phase difference. In a given image, the phase of each pixel is measured at each of a plurality of frequencies in a desired frequency range, typically 100 to 5,000 Hz and the median or average phase determined for the image at each frequency. In calculating the median or the average, the highest and lowest values are preferably excluded by using such methods as (1) including only pixels whose values lie within a specified range of the pixel histogram, such as only those between the 25 and 75 percentile phase values for the image. For each frequency, the median or average for the image is subtracted from the phase value for each pixel. This results in a phase difference spectrum which is positive for frequencies where the pixel value is higher than average and negative where it is lower. The sum of the phase differences is the integrated phase difference (IPD), and the sum of all the positive phase differences is the integrated positive phase difference. Both these measures are significantly higher for cancer than for normal surrounding tissues.

An eighth polychromic measure is the specific frequency. The phase of each pixel is measured at each of a plurality of frequencies in a desired frequency range, typically 100 to 5000 Hz. The resultant spectrum is fitted to a piecewise linear function, a spline function or a functional fit as known in the art. The lowest frequency at which the phase reaches 45 degrees is defined as the Specific Frequency. Specific Frequency is typically lower for cancer (range of 100 to 800 Hz) than for normal surrounding tissue (range of 1200 Hz to several kilohertz. The RC time constant evaluated at the specific frequency is also a useful related polychromic measure, being lower for cancer.

A ninth polychromic measure is the capacitance spectral slope, i.e., the derivative of the capacitance curve (or of the log capacitance curve), as a function of frequency, evaluated at a given frequency. This is considered to be a polychromic measure, since its determination requires the measurement of the capacitance at more than one point. Capacitance Spectral slope in the range 100 to 5000 Hz is typically negative and typically has a higher absolute value in cancer vs. normal pixels, particularly at low frequencies such as 100 to 500 Hz.

A tenth polychromic measure is the conductance spectral slope, the derivative of the conductance (or of the log conductance) evaluated at a given frequency. Conductance Spectral slope in the range 100 to 5000 Hz is typically positive and typically has a lower value in cancer vs. normal pixels, particularly at low frequencies such as 100 to 500 Hz.

The NIRD and PIRD measures may be defined in various ways. For example, the deviations from the representative value may be used in the calculation only when they exceed some minimum value. The deviation may be expressed as a the actual numerical deviation or more preferably as a ratio or as a deviation normalized to some "standard" deviation of the capacitance or conductance which is characteristic of normal tissue, as defined below.

Preferably, the value representative of normal tissue is derived by looking at pixel values representative of some proportion of the total number of pixels in an image. For example if a 8×8 image were used, and the anomalous portion occupied less than 25% of the image, the 16 pixels having each of the highest and the lowest values would not be considered. The representative value would then be, for example, the mean value of capacitance or conductance of the remaining pixels and a standard deviation would be the range of pixel values among the 32 pixels which are considered.

This determination is based on the practical consideration that almost always at least 50% of the pixels represent normal tissue. It is clear that many other measures of the representative value and of the "standard" deviation will be equally useful in the practice of the invention and that such measures may be computed in many different ways. Furthermore the range of pixels which are considered "normal" may be adjusted depending on the type of tissue actually being measured. For example, for tissue having large areas with apparently high values, a range of pixel values such as, for example 20%–50% (instead of the 25%–75% described above) may be more useful.

Another potentially useful polychromic parameter is the slope of the logarithm of the capacitance of a given pixel or region as a function of frequency. This curve generally has a shape which is predominantly linear. Alternatively, the ratio of the slope of the capacitance of the particular pixel to the slope of the capacitive representative value may be useful.

Furthermore, it may be useful to consider, as an additional polychromic measure, the maximum of one of the other polychromic measures, for example, the capacitance, conductance, Relative Difference Spectrum, Relative Ratio Spectrum, etc.

In general, some pixels are excluded from the characterization. These would include "No-Contact" pixels having near zero conductance and capacitance values and "Contact Artifactal Hot Spots" which are pixels, with elevated capacitance or conductance values, next to no contact pixels.

In impedance measurements of the breast in both men and women, normal breast tissue has a low capacitance and conductivity, except in the nipples, which have a higher C and G values than the surrounding tissue with the maximum obtained at the lowest frequency recorded, typically 100 Hz. The nipple capacitance and conductance remains very much higher than the surrounding tissue up to about 1400 Hz for fertile patients and up to about 2500 Hz for older patients (which is reduced to 1400 Hz for older patients by estrogen replacement therapy). These frequencies represent the normal range of spectral widths for the Relative and Difference Spectra. Tumors can be recognized by very high C and G relative ratio or relative difference values at all frequencies below 1000 Hz and moderate difference or ratio values for frequencies up to 2500 Hz or even higher.

Capacitance and conductance values are measured by comparing the amplitude and phase of the signal received by the sensing elements. Knowing both of these measures at the same points is useful to proper clinical interpretation. For example, as illustrated below in FIG. 14, a region of elevated conductivity and reduced capacitance (especially at relatively low frequencies, most preferably less than 500 Hz, by generally below 2500 Hz and also below 10 kHz) is associated with benign, but typically pre-cancerous atypical hyperplasia while, as shown in FIG. 15, cancer typically has both elevated capacitance and conductivity over, generally, a wide frequency range, as compared to the surrounding tissue. Proper differential diagnosis is aided by having the frequency samples be close enough together so that changes in the conductivity and capacitance in the low frequency range can be tracked. This also requires the display of both capacitance and conductance or the use of an impedance measure which is based on an appropriate combination of the two.

Methods for calculating C and G are given in the above-mentioned U.S. Pat. Nos. 4,291,708 and 4,458,694; the disclosures of which are incorporated herein by reference. A preferred embodiment of the invention takes advantage of the calibration capability inherent in the use of cover plates as shown in FIGS. 5A and 5B. It can be shown that if the received waveform is sampled at a fixed spacing, δ, such that N samples are taken in each cycle, then the real and imaginary values of the impedance can be determined as:

$$G = \Sigma(g_n(V_{(n+\frac{1}{2}N)} - V_n),$$

and $$(1) C = \Sigma(c_n(V_{(n+\frac{1}{2}N)} - V_n),$$

where $g_n$ and $c_n$ are constants determined by a calibration procedure and $V_n$ is the voltage measured at the nth sampling point (out of N). The first sample is taken at zero phase of the reference signal.

One relatively easy way to determine the constants is to perform a series of measurements when cover plate is in contact with the sensing elements as described above and a known impedance is placed between the transmitter and the cover plate. Since N coefficients are required for determining $g_n$ and $c_n$ for each frequency, N values of admittance and N measurements are required. For example, if N=4 (four samples per cycle) four different measurements are taken and the sampled signal values are entered into the above equations to give N equations, which are then solved for the values of the coefficients. The higher the number of samples, the greater the accuracy and noise immunity of the system, however, the calibration and computation times are increased.

Alternatively, fewer samples are taken and values for a number of measurements are averaged, both in the calibration and clinical measurements to reduce the effects of noise.

Artifactal abnormalities in the impedance image can be caused by such factors as poor surface contact or insufficient conductive coupling on some or all of the sensing elements, the presence of air bubbles trapped between probe and tissue and normal anatomical features such as bone or nipple.

Bubbles can be recognized by their typically lower C and G values compared to background, often immediately surrounded by pixels with much higher C and G. Bubbles can be verified and eliminated by removing the probe from the skin and repositioning it, and or by applying additional conductive coupling agent. Contact artifacts can be determined and accounted for in real time by translating the probe and viewing the image as described above. Artifacts either disappear or remain fixed with respect to the pixels, while real tissue features move, on the image, in a direction opposite from the motion of the probe. Additionally, as described above, if the tissue beneath the skin is physically moved, while the probe and skeletal structure is kept fixed, only real tissue features will move. If the feature remains static, it is either a skin feature or bone.

If as described above, the probe and the tissue are moved together without moving the underlying structure (such as the bones). Tissue lesions and surface effects will remain relatively stationary in the image while bone artifacts will move in the opposite direction, thus distinguishing them from other impedance deviations.

Figure 14:
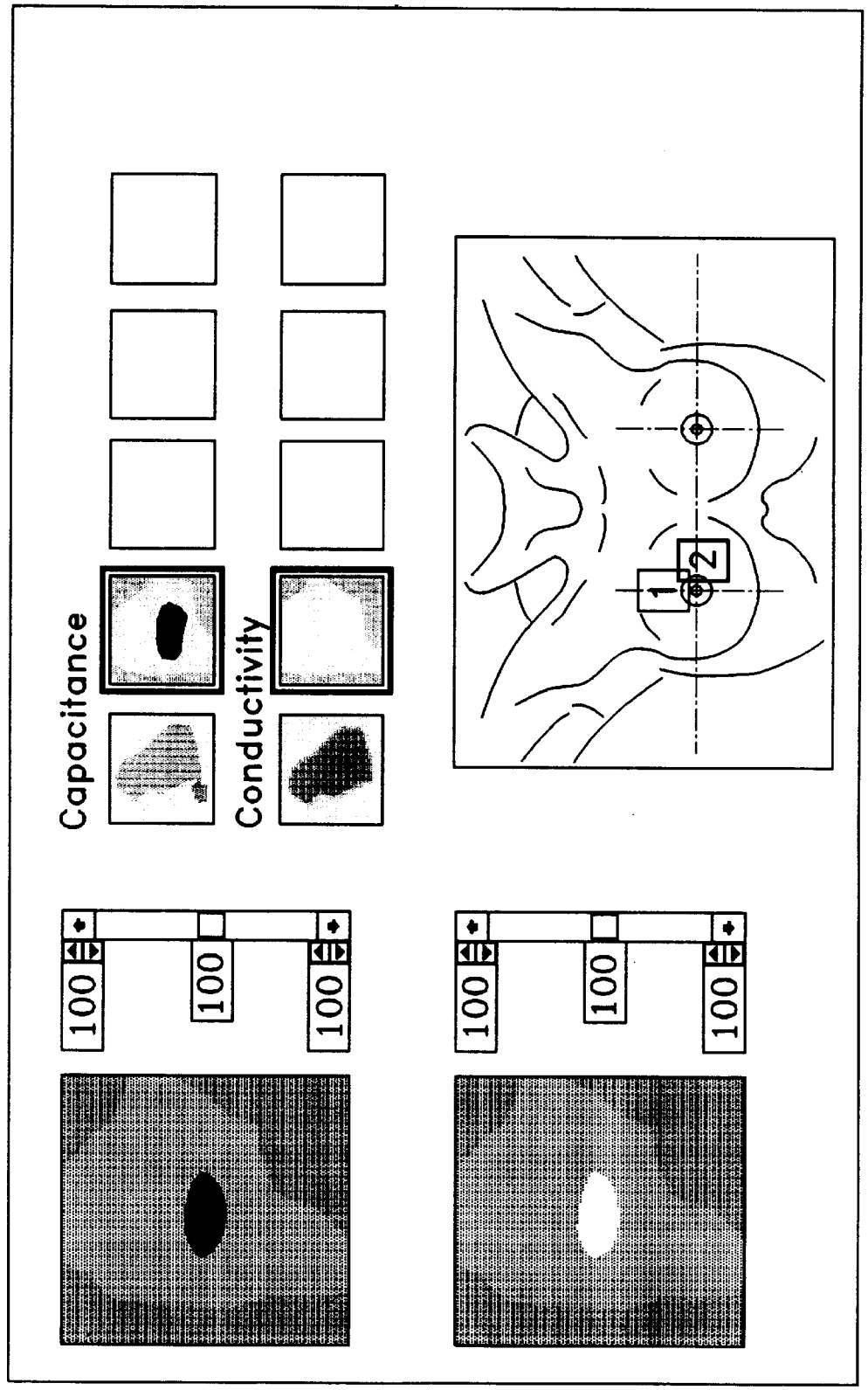
FIG. 14 illustrates a display, according to a preferred embodiment of the invention showing both capacitive and conductance images illustrative of atypical hyperplasia.
Figure 15:
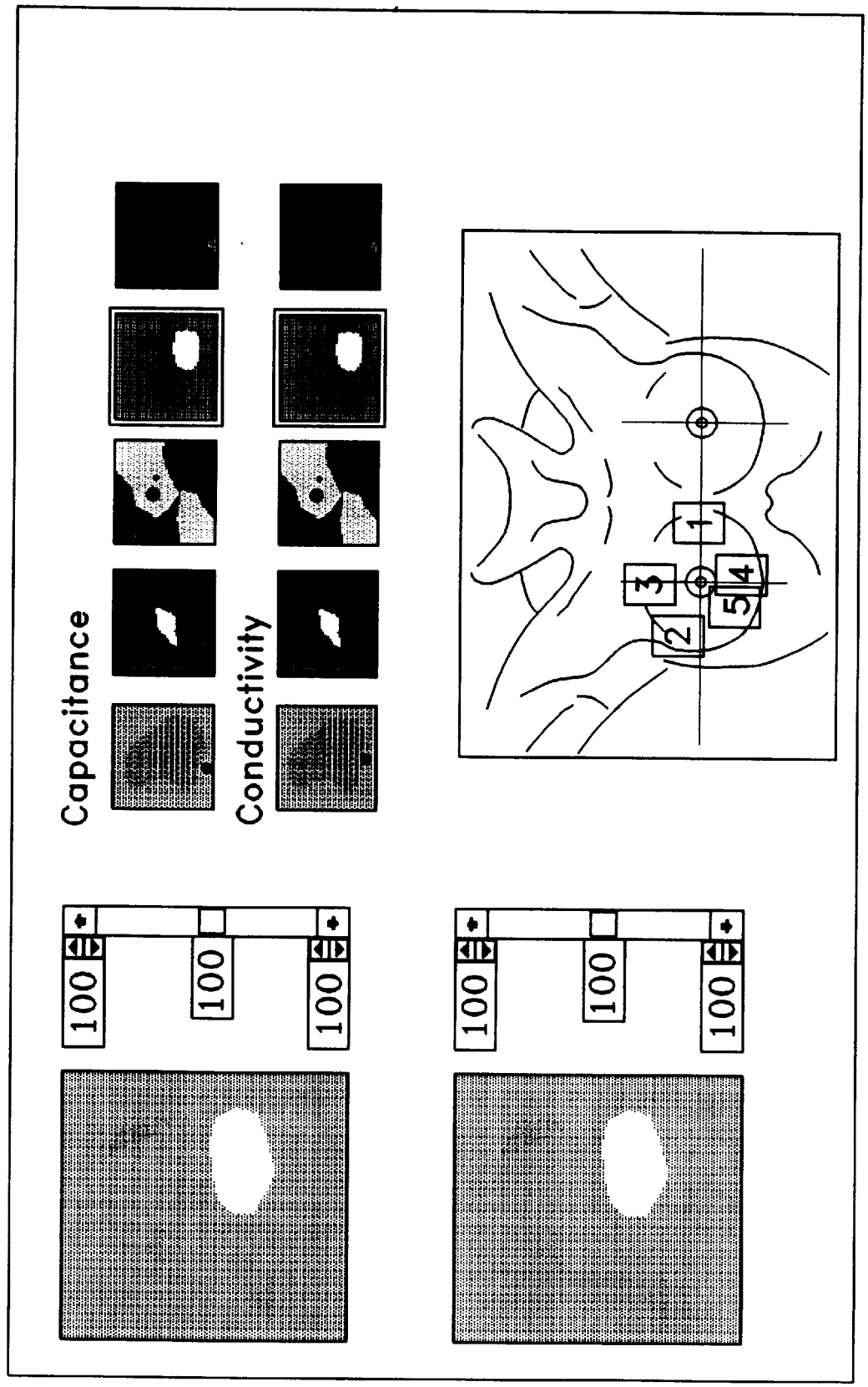
FIG. 15 illustrates a display, according to a preferred embodiment of the invention showing both capacitive and conductance images illustrative of a carcinoma.

FIG. 14 shows one example of a display, according to a preferred embodiment of the invention. In this display, capacitance and conductivity images at two positions on a breast are shown, together with an indication of the positions on the breast at which these images were acquired.

In particular, as seen in FIG. 15, the display includes the capability of displaying up to five sets of capacitance and conductance images in the five sets of smaller squares. These images are associated with probe areas indicated as numbers 1–5 on the breast image shown in the display. In practice, the examiner manipulates a joystick or other digital pointing device, such as device 105 shown in FIG. 6A. This device is manipulated until a square is appropriately placed on the breast image. The examiner then presses a button which causes a pair of impedance images to be stored and displayed on the screen in an appropriate square, and the indicated position to be displayed on the physiological (breast) drawing. The small images are numbered from left to right. Preferably, the examiner can scale the physiological image so that the dimensions of the breast shown and the extent of the probe array are compatible. It should be understood that during the placement of the probe, real time images (acquired about once every 50–80 msec) of the capacitance and the conductance are shown, for example in the large squares to the left of the display.

FIG. 14, which represents an actual imaging situation shows, in the leftmost of the small images, a situation in which a small atypical hyperplasia which was previously detected by other means. This position shows an elevated conductivity and a very slightly reduced capacitance. In position 2, which is also shown in the two large squares to the right of the display, a previously unsuspected area having a capacitance/conductance profile characteristic of atypical hyperplasia is detected.

FIG. 15 shows a study typical of multiple suspected sites of carcinoma (in positions 2 and 4). The images of position 4 are shown in enlarged format at the left of the image. In these sites, both the capacitance and conductance are elevated with respect to their surroundings.

Alternatively, a composite image such as the image of the sum of the capacitance and conductance images, their product, their sum or their ratio can be displayed to give a similar indication of the type of detected anomaly. A color coded composite image can also be displayed, where, for example, the median value for each image would be black and where positive and negative values would have a particular color which, when combined would result in distinctive colors for suspect impedance deviations.

The display shown in FIGS. 14 and 15 can be utilized to show a plurality of images of the same region at a plurality of frequencies. Alternatively or additionally, the display can be utilized to show a plurality of different polychromic measures of the same region. In addition, using, for example, the fact, as described below with an example, that a plurality of such measures can be useful in identifying tissue type more accurately than can a single measure, the display may include, inter alia, an image in which portions of the image is identified by tissue type. For such an image, for example, the color of portions of the map could represent the type of tissue and the brightness the certainty of the identification. The type identification and certainty would depend on the probability that a particular "mix" of values of the polychromic measures are associated with a particular tissue type and that not all measures are always within the specified range for any particular tissue type. In conjunction with the display of such a map the individual polychromic measures may be displayed either together or in sequence to make the determination of the tissue type more certain.

One type of display of multiple polychromic images is to use a pseudo color image of two or three colors, each of which represents one of the measures. When a measure for a portion of the image meets the criteria for a given tissue type it is displayed in its assigned color. When two or more such criteria are met a different color is displayed, depending on which of the criteria are met.

Another type of display shows the values of the measures as iso-contours of varying brightness of a color assigned to the measure. The conjunction of isocontour lines characteristic of a given tissue type may then be recognized from isocontours.

Alternatively or additionally, the image can be a pseudo 3-D image wherein each of the measures is delineated as a wire screen of a given color. This allows for the visualization of more than one measure at the same time.

Alternatively, a map of immitance, or the real or imaginary part thereof is overlaid with indications, based on polychromic measures of the tissue type involved, as for example by color coding, by arrows with associated legends or by other means to alert the operator to suspected sites of tissue of specific types. Such measures may be calculated automatically or in response to a query from the operator in respect to an area of the image of which he is suspicious.

It has been found that certain immitance measures and combinations of measures are characteristic of certain types of normal and abnormal tissue. In one example of the method four of the polychromic measures described above can be utilized separately or, more particularly, in combination to indicate the presence of certain normal or abnormal tissue. These four measures are CFX, G-PIRD, C-PIRD and C-NIRD measure. Other combinations of polychromic measures are also useful in indicating tissue type.

It has been found that normal tissue, as expected, has low or zero values of all of the measures. Nipples and the infra-mammary ridge have a very high value of G-PIRD and C-PIRD together with zero to low value of CFX and no G-NIRD. Ribs and the costo-chondral junction have low values of C-PIRD and CFX, moderate to high values of G-PIRD and low values of C-NIRD. Typical benign hyperplasia has a moderate to high value of C-NIRD and G-PIRD, a high value of CFX and no C-PIRD, while precancerous atypical hyperplasia has values in a range similar to that of typical hyperplasia for C-NIRD, and G-PIRD but has a moderate value of CFX and C-PIRD. This allows precancerous atypical hyperplasia to be differentiated from benign hyperplasia. Furthermore, cancerous tumors appear to be characterized by medium to high values of C-PIRD and CFX, high values of G-PIRD and low values C-NIRD. Some tumors, especially those with very high C-PIRD have no C-NIRD.

Figure 18A:
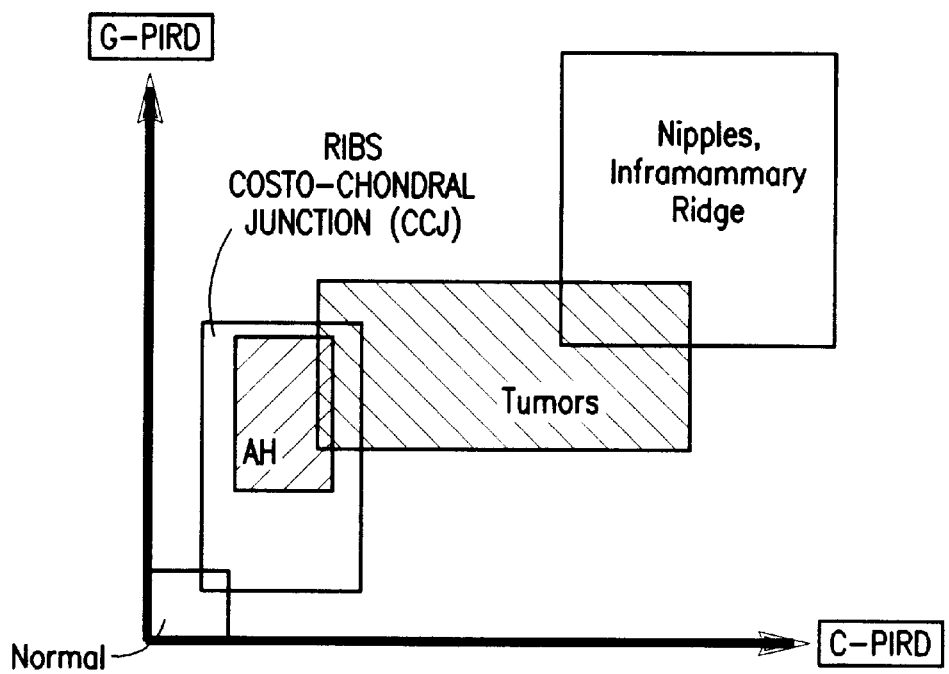
FIGS. 18A–18C show maps of polychromic measures characteristic of certain tissue types.
Figure 18B:
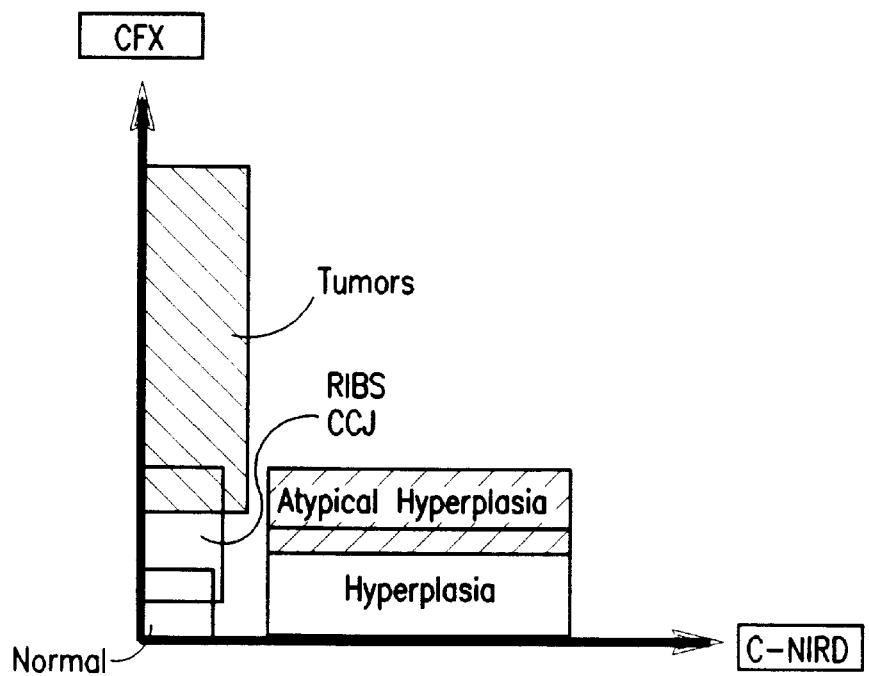
Figure 18C:
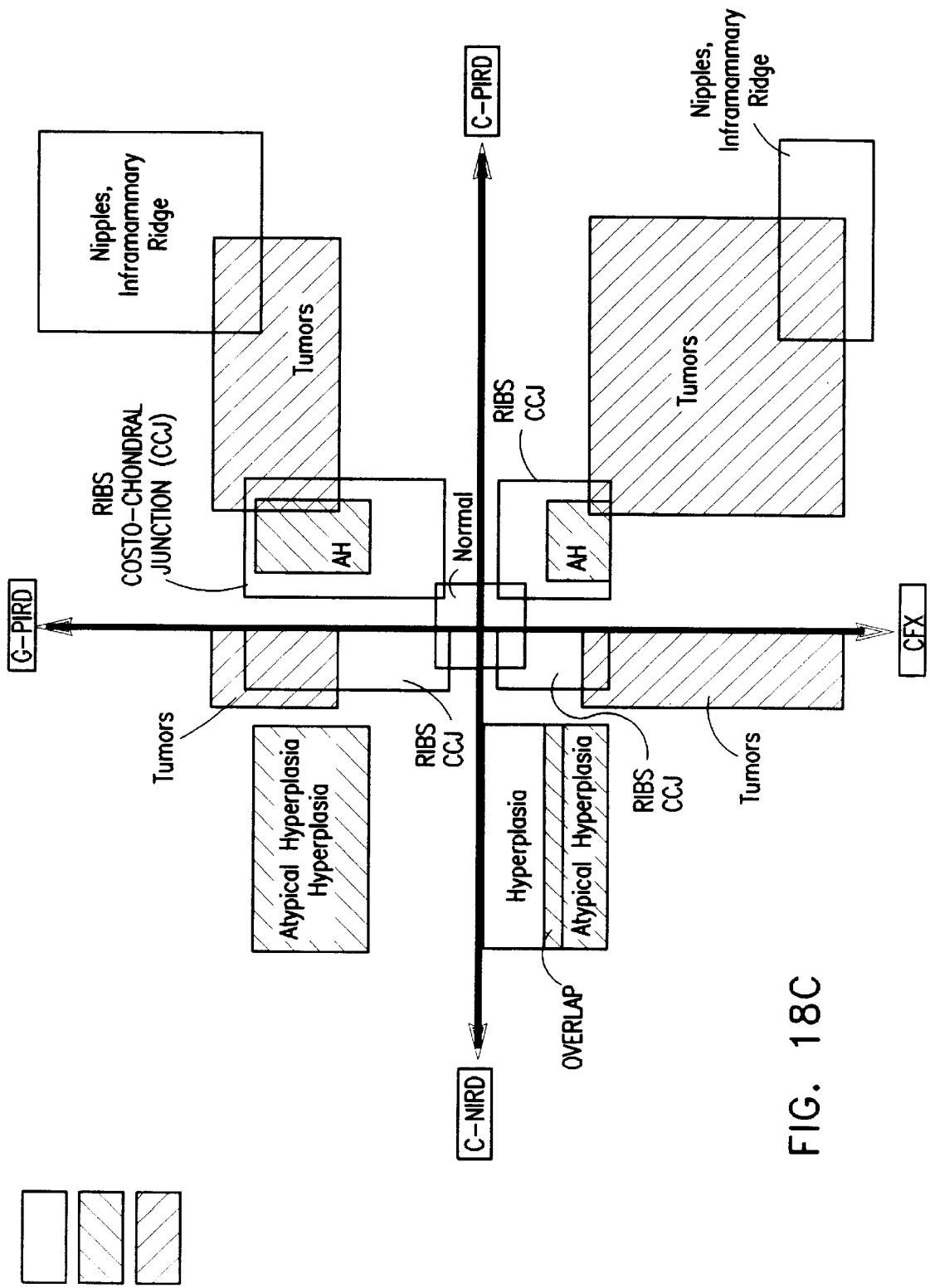

The four measures, C-PIRD, C-NIRD, G-PIRD and CFX, form a four dimensional space in which each set of measurements in designated by a single point. In order to represent such a space on paper two orthogonal projections of the four dimensional space are required. One such set of orthogonal projections is shown in FIGS. 18A and 18B. While these projections fully describe all four measures, they plot the measures in pairs only. Presenting the regions of the space which are characterized by the various tissue types in a single drawing is possible since all of the measures have only positive (or zero) values. Since only positive values of the measures are allowed it is possible to combine these two orthogonal projections, as in FIG. 18C, into a single projection in which each of the axes represents a positive value of one of the measures. FIG. 18C shows the information in a redundant manner (i.e., it actually shows two orthogonal projections), however, it is useful since it shows all combinations of the various measures on a single figure.

It will be noted from FIGS. 18A–C and from the above discussion that there is some overlap between nipples (and Infra-mammary ridge) and tumors and also between ribs (and costo-chondral junction) and tumors. Where ambiguity does exist (i.e., in the relatively small overlap areas shown in FIG. 18C) the distinction can generally be made based on the anatomy of the portion of the patient being imaged. Thus, an ambiguous tumor/nipple far from the nipple would be classified as a tumor and a tumor/rib far from the ribs would be classified as a tumor. Where the anatomy does not allow for a clear determination, such as for example a tumor which is close to the nipple, an additional view and/or a different breast position, palpation or other methods of separating the anomaly from the normal tissue will generally remove the ambiguity.

While a particular impedance imaging system has been described as the basis for determining the type of tissue underlying the anomalies (and causing them) The method is also believed to be generally useful in tissue type determination using other types of impedance imaging systems and also in situations where no image is generated.

For example, the method is also potentially useful to determine tissue types in situations where either a single impedance probe is used or where the image is small and only anomalous areas are imaged. In these cases the comparison for determining the measures is made between the values of capacitance or conductance measured for the anomalous region as compared to the capacitance or conductance measured for a nearby region known to be normal.

The method is also useful for determining the type of tissue which is pierced by a biopsy needle or contacted directly by a probe such as the finger probe of FIG. 7A of the invasive probes of FIGS. 8–10. In these cases a comparison may be made between values at the tissue to be characterized and other "normal" tissue.

Figure 17A:
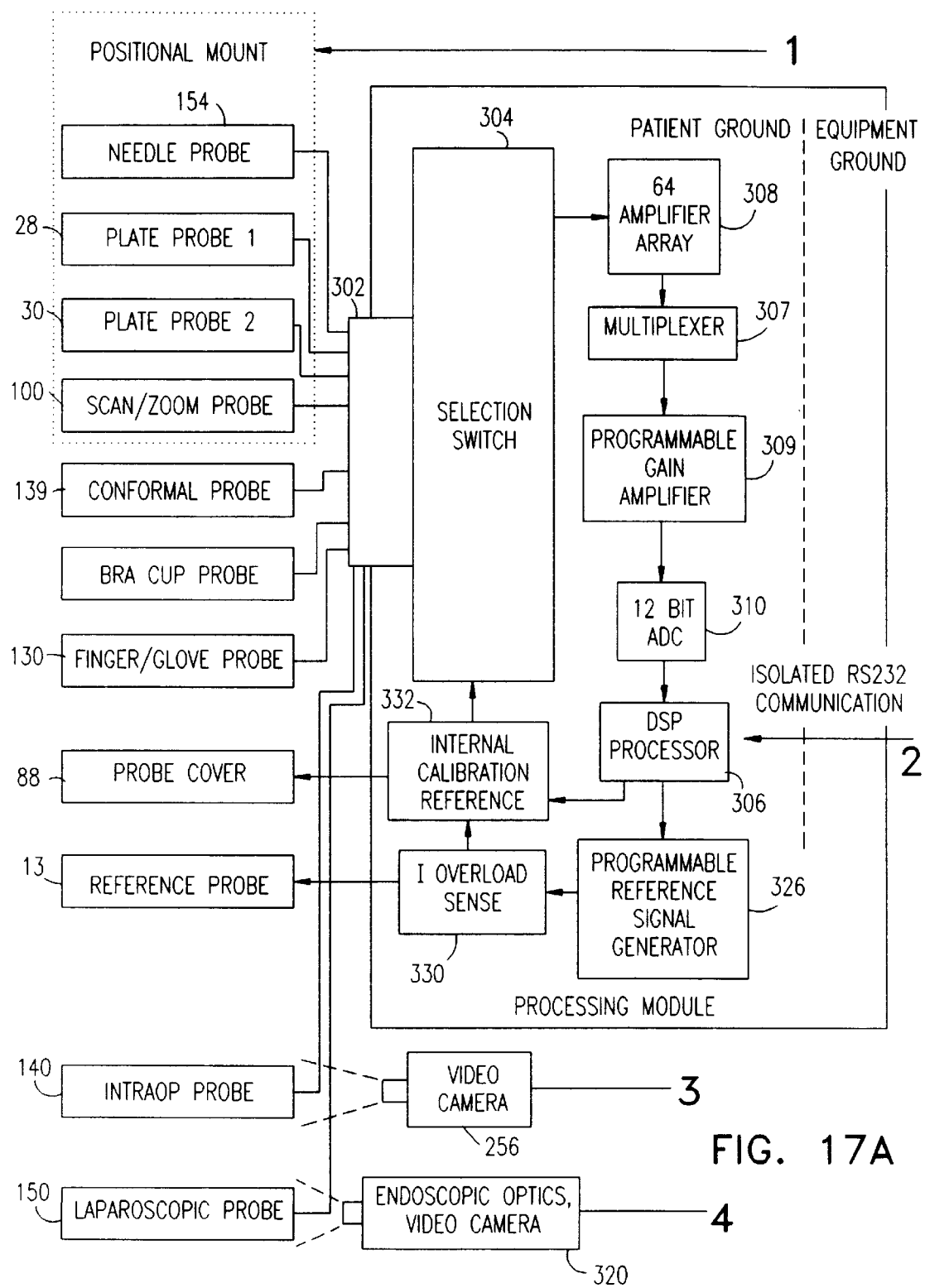
FIGS. 17A and 17B are a block diagram of circuitry suitable for impedance mapping in accordance with a preferred embodiment of the invention.
Figure 17B:
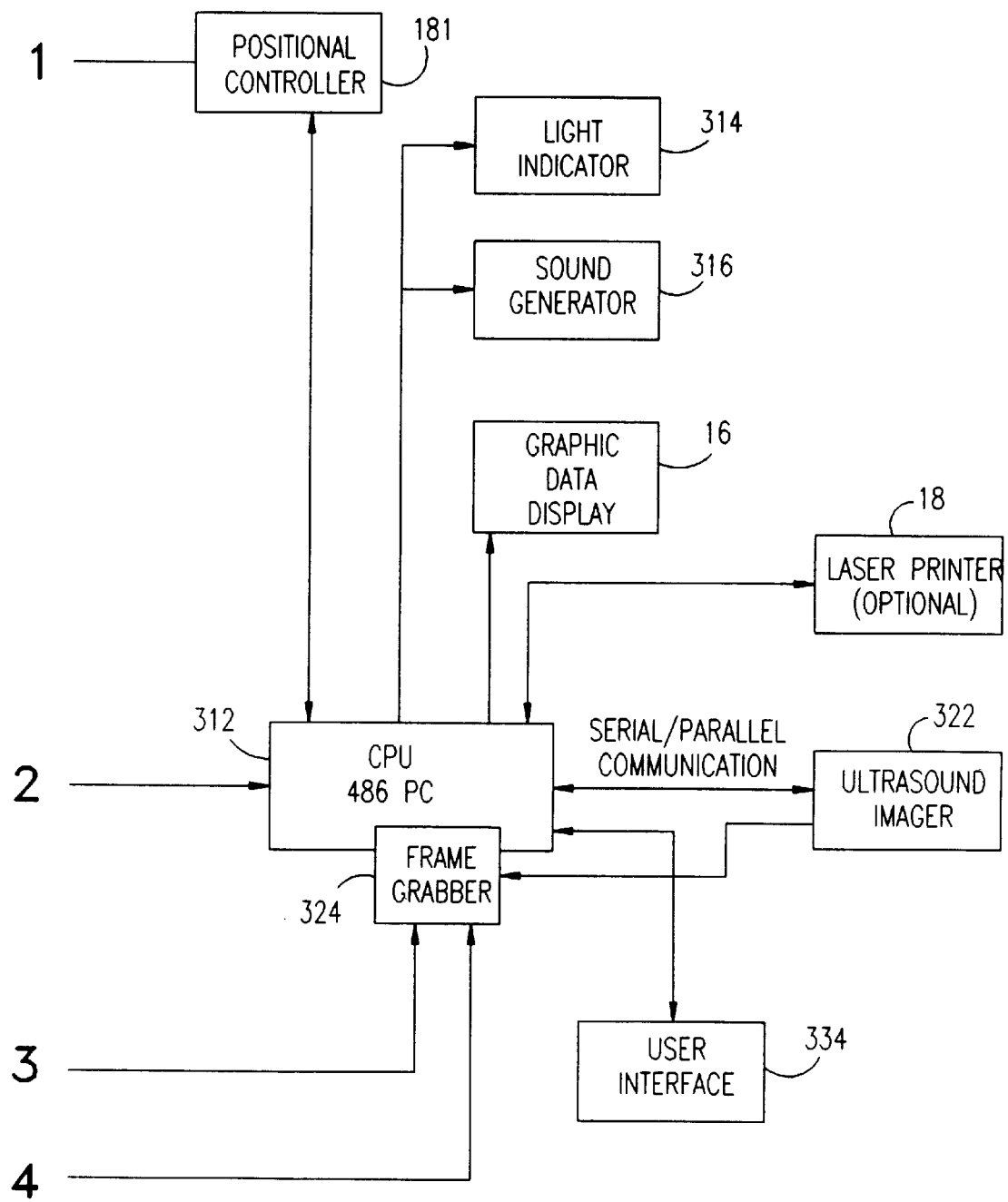

FIGS. 17A and 17B show a block diagram of a preferred embodiment of a system 200 which incorporates a number of multi-element probes. It should be understood that the exact design of system for impedance imaging will depend on the types of probes attached to the system and the exact imaging modalities (as described above) which are used.

As shown in FIGS. 17A and 17B the preferred system can incorporate biopsy needle probe 154, two plate probes 28, 30 such as those shown in FIGS. 1–3, scan zoom probe 100 such as that shown in FIG. 6A, conformal probe 139 such as that shown in FIG. 7B, a bra-cup probe, finger/glove probe 130 such as that shown in FIG. 7A, laparoscopic probe 150 such as that shown in FIG. 9 or an intra-operative probe 140 as shown in FIG. 8. Furthermore, when three probes are used as in FIG. 11E, provision is made for attachment of a third plate probe. The position of the plate and needle probes is controlled by controller 181 as described in respect to FIG. 11D.

The probes as connected via a series of connectors, indicated by reference numeral 302 to a selection switch 304 which chooses one or more of the probes in response to a command from a DSP processor 306. Selection switch 304 switches the outputs of the probes, namely the signals detected at the sensing elements of the probes (or amplified versions of these signals) to a set of 64 amplifiers 308, one amplifier being provided for each sensing element. For those probes, such as the large plate probes, which have more than 64 sensing elements, the selection switch will (1) sequentially switch groups of 64 sensing elements to amplifier set 308, (2) choose a subset of sensing elements on a coarser grid than the actual array by skipping some elements, as for example every second element, (3) sum signals from adjacent elements to give a new element array of lower resolution and/or (4) choose only a portion of the probe for measurement or viewing. All of these switching activities and decisions are communicated to the switch by DSP processor 306 which acts on command from a CPU 312. The output of the amplifiers is passed to a multiplexer 307 where the signals are serialized prior to conversion to digital form by a, preferably 12-bit, A/D convertor 310. A programmable gain amplifier 309, preferably providing a gain which is dependent on the amplitude of the signals, is optionally provided to match the signal to the range of the A/D convertor. The output of A/D 310 is sent to the DSP for processing as described above. In a preferred embodiment of the invention DSP 306 is based on a Motorola MC 68332 microprocessor.

While 64 amplifiers has been chosen for convenience and lower cost, any number of amplifiers can be used.

The DSP calculates the impedance results and send the results to CPU 312 for display on a graphic data display 16, printing on a printer 18 or other output signals generation as described above by a light indicator 314 or a sound indicator 316.

Alternatively, the DSP directs signal sampling and averages together the samples or pre-processes them, sending the averaged or pre-processed samples to CPU 312, which then performs the impedance calculations.

The CPU may also receive images from video camera 256, for example, when used with an intra-operative probe, from an endoscopic optics and camera system 320, for example when the camera views the outer surface of the laparoscopic probe or from an ultra sound imager 322, for example, in biopsy performance as shown in FIGS. 11A and 11B. When an image is acquired from one of these cameras a frame grabber 324 is preferably provided for buffering the camera from the CPU. As described above, the CPU combines these images with the impedance images provided by one or more probes for display or other indication to the operator.

FIG. 15 also shows a programmable reference signal generator 326 which receives control and timing signals from the DSP. The reference signal generator generates excitation signals which are generally supplied, during impedance imaging, to reference probe 13, which, as described above, is placed at a point (or at more than one point) on the body remote from the region of impedance measurement. Signal generator 312 may produce a sinusoidal waveform, pulses or spikes of various shapes (including a bipolar square shape) or complex polychromic waveforms combining desired excitation frequencies. Appropriate impedance calculations, in DSP 306 or in CPU 312, are implemented in accordance with the waveform of the excitation.

Where a breast is imaged and one of the two plates is used as the source of excitation, as described above, the output of signal generator is sent to the exciting plate (signal paths not shown for simplicity). A current overload sensor 330 is preferably provided after the signal generator to avoid overloads caused by short circuits between the reference probe and the imaging probe or ground.

Also shown on FIG. 17A is an internal calibration reference 332 which is preferably used for internal calibration of the system and for testing and calibration of the probes.

For internal testing and calibration, calibration reference 232 receives the signals generated by the programmable reference signals generator as passed to the selection switch, in series with an internal admittance in the calibration reference, as selected by the DSP processor. The DSP processor computes the admittance from signals received from the A/D convertor and compares the computed admittance with the actual admittance provided by internal calibration reference 332. This comparison can be provide an indication that the system requires adjustment or repair or can be used to calibrate the system.

Similarly, the output of calibration reference 332 may be provided to probe cover 88 for calibration and quality assurance of a plate or scan probe as described above. Under this situation, the DSP instructs selection switch 304 to choose the input from the respective probe.

Also provided is a user interface 334 such as a keyboard, mouse, joystick or combinations thereof, to allow the operator to enter positional information via the screen and to choose from among the probes provided and from the many options of calculation, display, etc.

Although described together as the preferred embodiment of the invention, it is not necessary to use the probes of the invention, the methods of calculation of impedance and impedance characteristics of the invention and the preferred apparatus of the invention together. While it is presently preferred that they be used together they may each be used with probes, calculation methods and apparatus for impedance imaging as applicable and as available.

Certain aspects of the invention have been described with respect to a biopsy needle or with respect to placement of such a needle. It should be understood that such description and aspects of the invention are equally applicable to positioning needles, catheters, endoscopes, etc.

Although various embodiments, forms and modifications have been shown, described and illustrated above in some detail in accordance with the invention, it will be understood that the descriptions and illustrations are by way of example, and that the invention is not limited thereto but encompasses all variations, combinations and alternatives falling within the scope of the claims which follow:

What is claimed is:

1. A multi-element probe for providing an electrical connection to a tissue surface including:

a plurality of individual conductive sensing elements, each having a front portion suitable for contact with the tissue surface; and finger mounting apparatus, said sensing elements being attached to the outside of the apparatus, such that the sensing elements face outwards;

the sensing elements being mounted such that a wearer of the apparatus can perform palpative examination concurrently with impedance imaging.

2. The probe of claim 1 further including a plurality of conductive elements providing an electrical connection to the respective individual sensing elements.

3. The probe of claim 2 further including a partition separating the individual sensing elements such that when the individual probes contact the tissue surface they are substantially electrically isolated from each other.

4. The probe of claim 3 wherein each individual sensing element is located in a well formed by the partition and a substrate underlying the sensing element.

5. The probe of claim 4 wherein the well is formed by embossing the partition on a sheet of material, whereby the un-embossed portion of the sheet forms the substrate underlying the sensing element.

6. The probe of claim 4 wherein the well is formed by laminating a grid formed by holes punched in a sheet or formed by extrusion to the substrate.

7. The probe of claim 4 wherein the well is formed by printing the partitions onto the substrate.

8. The probe of claim 3 wherein the sensing elements do not extend past the top of the partition.

9. The probe of any of claims 1–8 wherein the sensing elements comprise a conductive, viscous gel.

10. The probe according to any of claims 1–8 wherein the sensing elements comprise a conductive, flexible solid.

11. The probe according to any of claims 1–8 wherein the sensing elements comprise a sponge impregnated with a conductive viscous gel.

12. The probe according to any of claims 1–8 wherein the sensing elements are formed on a flexible surface, whereby the multi-element probe conforms, at least in part, to the tissue.

13. The multi-element probe according to any of claims 1–8 wherein the finger mounting apparatus includes a glove having fingers, said sensing elements being attached to a finger thereof.

14. A method comprising:

providing an impedance measurement system including a multi-element probe attached to at least one finger of an examiner; and providing an indication of impedance generated on the basis of signals detected by said elements.

* * * * *